US008192404B2

(12) United States Patent
Murashita et al.

(10) Patent No.: US 8,192,404 B2
(45) Date of Patent: Jun. 5, 2012

(54) INDWELLING NEEDLE ASSEMBLY

(75) Inventors: Takato Murashita, Nakakoma-gun (JP);
Junichi Ogawa, Nakakoma-gun (JP);
Ryoji Kobayashi, Nakakoma-gun (JP)

(73) Assignee: Terumo Kabushiki Kaisha, Tokyo (JP)

( * ) Notice: Subject to any disclaimer, the term of this patent is extended or adjusted under 35 U.S.C. 154(b) by 168 days.

(21) Appl. No.: 12/091,369

(22) PCT Filed: Oct. 23, 2006

(86) PCT No.: PCT/JP2006/321075
§ 371 (c)(1),
(2), (4) Date: Aug. 12, 2008

(87) PCT Pub. No.: WO2007/049564
PCT Pub. Date: May 3, 2007

(65) Prior Publication Data
US 2008/0312596 A1  Dec. 18, 2008

(30) Foreign Application Priority Data
Oct. 25, 2005  (JP) .................................. 2005-310491

(51) Int. Cl.
*A61M 5/178* (2006.01)
(52) U.S. Cl. ..................... 604/167.01; 604/44; 604/508; 604/167.03; 604/167.06; 604/264; 604/45; 604/272; 604/403; 604/513; 604/167.02; 604/167.04; 604/167.05
(58) Field of Classification Search .................... 604/44, 604/45, 508, 167.03, 167.06, 264, 272, 403, 604/513, 167.01–167.07
See application file for complete search history.

(56) References Cited

U.S. PATENT DOCUMENTS 3,463,152 A * 8/1969 Sorenson ....................... 604/162
4,676,783 A * 6/1987 Jagger et al. .................. 604/171
(Continued)

FOREIGN PATENT DOCUMENTS
EP  0256694 A1  2/1988
(Continued)

OTHER PUBLICATIONS

Form PCT/ISA/210 (International Search Report) dated Jan. 23, 2007.

(Continued)

*Primary Examiner* — Jackie Ho
*Assistant Examiner* — Scott Medway
(74) *Attorney, Agent, or Firm* — Buchanan Ingersoll & Rooney PC

(57) ABSTRACT

An indwelling needle assembly includes a stylet having a sharp needlepoint at an end thereof, a stylet hub secured to a base end of the stylet, a hollow outer needle in which the stylet is inserted, an outer needle hub secured to a base end of the outer needle, an opening formed at the base end or at a side of the outer needle hub to communicate with the inner cavity of the outer needle, a seal fitted onto the outer needle hub and in which a hole or slit is provided for insertion of the stylet therein, the hole or slit being formed to become closed when the inserted stylet is extracted, an operating part installed on the outer needle hub to move the stylet and outer needle along the longitudinal direction when the stylet is inserted into the outer needle, and a movement suppresser for stopping or suppressing moving the stylet relative to the seal when the operating part is operated.

8 Claims, 12 Drawing Sheets

U.S. PATENT DOCUMENTS

| | | | | |
|---|---|---|---|---|
| 4,781,692 A | * | 11/1988 | Jagger et al. | 604/164.08 |
| 4,828,547 A | * | 5/1989 | Sahi et al. | 604/110 |
| 4,960,412 A | * | 10/1990 | Fink | 604/167.04 |
| 5,088,982 A | * | 2/1992 | Ryan | 604/110 |
| 5,169,391 A | * | 12/1992 | Vogel | 604/177 |
| RE34,416 E | * | 10/1993 | Lemieux | 604/164.08 |
| 5,549,571 A | * | 8/1996 | Sak | 604/198 |
| 5,603,706 A | * | 2/1997 | Wyatt et al. | 604/539 |
| 5,743,882 A | * | 4/1998 | Luther | 604/164.05 |
| 5,935,110 A | | 8/1999 | Brimhall | |
| 5,967,490 A | * | 10/1999 | Pike | 251/149.1 |
| 6,221,050 B1 | | 4/2001 | Ishida | |
| 6,352,521 B1 | * | 3/2002 | Prosl | 604/167.03 |
| 6,749,588 B1 | * | 6/2004 | Howell et al. | 604/164.08 |
| 6,878,134 B2 | * | 4/2005 | Rogers et al. | 604/164.01 |
| 7,329,238 B2 | * | 2/2008 | Halseth et al. | 604/110 |
| 7,470,254 B2 | * | 12/2008 | Basta et al. | 604/167.04 |
| 2004/0068232 A1 | * | 4/2004 | Hart et al. | 604/167.06 |
| 2005/0192535 A1 | | 9/2005 | Takagi et al. | |
| 2006/0253076 A1 | * | 11/2006 | Butts et al. | 604/167.06 |

FOREIGN PATENT DOCUMENTS

| | | |
|---|---|---|
| JP | 2-147137 U | 12/1990 |
| JP | 8-257129 A | 10/1996 |
| JP | 10-179734 A | 7/1998 |
| JP | 10-272182 A | 10/1998 |
| JP | 2000-279527 A | 10/2000 |
| JP | 2005-065993 A | 3/2005 |
| JP | 2005-261931 A | 9/2005 |
| JP | 2005-261938 A | 9/2005 |

OTHER PUBLICATIONS

Non-English language version of Form PCT/ISA/237 (Written Opinion of the International Searching Authority) dated Jan. 23, 2007.

Office Action issued Apr. 4, 2010 by the Patent Office of the People's Republic of China in Chinese Patent Application No. 200680040102.X and partial English language translation.

Front page of the patent publication issued on Feb. 8, 2012 in corresponding Chinese Patent Application No. 200680040102.X, and a partial translation of the Patent Publication.

* cited by examiner

INDWELLING NEEDLE ASSEMBLY

TECHNICAL FIELD

The present invention relates to an indwelling needle assembly made to puncture a blood vessel and indwell within the blood vessel when performing an infusion, for example.

BACKGROUND ART

In the case an infusion is carried out on a patient, or for similar occasions, an indwelling needle connected to an infusion line is made to puncture a blood vessel and indwell within the blood vessel.

Such an indwelling needle includes a hollow outer needle, an outer needle hub secured to a base (proximal end) of the outer needle, a stylet having a sharp needlepoint at its tip (distal end) which is inserted into the outer needle, and a stylet hub secured to the base of the stylet (refer, for example, to Japanese Laid-Open Patent Publication No. 10-179734).

At the time of making the indwelling needle puncture the patient's blood vessel, the stylet is inserted into the outer needle, while the needlepoint of the stylet protrudes from the tip of the outer needle. In such an assembled condition, a puncturing operation is carried out, wherein normally, the outer needle hub is connected to a connector of the infusion line.

Then, when the needlepoint of the stylet has reached the inside of the blood vessel, blood flowing through the opening at the needlepoint passes through the inner cavity of the stylet, and flows into an interior region of the transparent stylet hub (flashback). This makes it possible to confirm (visually check) that the blood vessel has been accessed by the stylet.

After confirmation of flashback, the outer needle is advanced as a guiding stylet, so as to insert the outer needle into the blood vessel (to achieve puncture).

Next, while gripping the outer needle by hand, the stylet is pulled out of the outer needle. Then, an infusion liquid is infused through the connected infusion line and the outer needle.

Meanwhile, the outer needle hub is provided with vanes as an operating part thereof. When the stylet and the outer needle are made to puncture the living body, the indwelling needle assembly is placed in an assembled condition, and a puncturing operation is carried out on the skin while pinching the vanes with the fingers.

However, the indwelling needle assembly described in Patent Document 1 has a problem in that, at the time the puncturing operation is performed, the stylet may be pushed back by the skin before the skin is punctured and retracted into the outer needle, i.e., operability of the puncturing operation may be poor.

DISCLOSURE OF THE INVENTION

It is an object of the present invention to provide an indwelling needle assembly, which is excellent in operability at the time a puncturing operation is performed.

In order to attain the above object, according to the present invention, there is provided an indwelling needle assembly including:

a stylet having a sharp needlepoint at its tip,
a stylet hub secured to a base end part of the stylet,
a hollow outer needle in which the stylet is inserted,
an outer needle hub secured to a base end part of the outer needle,
an opening formed at a base end part or a side part of the outer needle hub, so as to communicate with an inner cavity of the outer needle,
a seal member provided at the outer needle hub, and in which a hole or a slit for inserting the stylet therein is formed, the hole or slit becoming closed when the inserted stylet is extracted,
an operating part provided at the outer needle hub for enabling movement of the stylet and the outer needle along a longitudinal direction in an inserted condition in which the stylet is inserted in the outer needle, and
movement suppressing means for inhibiting or suppressing movement of the stylet relative to the seal member when the operating part is operated.

According to the present invention, excellent operability is ensured when a puncturing operation is carried out.

In addition, in the indwelling needle assembly of the present invention, preferably, a tube is connected to the opening.

This ensures that a liquid can be supplied through the tube and into the outer needle.

In addition, in the indwelling needle assembly of the present invention, preferably, the tube is inserted into the stylet hub.

This ensures that the tube can be prevented from posing an obstacle during operation of the indwelling needle assembly.

In addition, in the indwelling needle assembly of the present invention, preferably, the movement suppressing means is composed of a varied outer diameter part, which is disposed on an outside surface of the stylet, wherein the outer diameter of the stylet is varied abruptly so that frictional resistance between the outside surface of the stylet and the inside surface of the hole or slit is increased.

This results in increasing the frictional resistance between the outside surface of the stylet and the inside surface of the slit (or hole) when the puncturing operation is conducted. Therefore, a problem wherein the stylet is pushed by the skin and retracted into the outer needle before the skin is punctured can be prevented or restrained, so that the stylet punctures the skin reliably. In other words, the indwelling needle assembly is excellent in operability at the time the puncturing operation is carried out.

Further, in the indwelling needle assembly of the present invention, preferably, the varied outer diameter part is composed of a plurality of minute projections, which project from the outside surface of the stylet.

This leads to an increase in the frictional resistance between the outside surface of the stylet and the inside surface of the slit (or hole). Therefore, the problem wherein the stylet is pushed by the skin and retracted into the outer needle before the skin is punctured can be prevented or restrained, so that the stylet punctures the skin reliably. In other words, the indwelling needle assembly is excellent in operability at the time the puncturing operation is carried out.

In addition, in the indwelling needle assembly of the present invention, preferably, the movement suppressing means is configured such that the extent of the inhibition or suppression of movement of the stylet differs, depending on whether the movement of the stylet is a distal movement or a proximal movement.

This permits easy insertion of the stylet into the seal member, for example, during manufacturing of the indwelling needle assembly. It also ensures that the problem wherein the stylet is pushed by the skin and retracted into the outer needle before the skin is punctured can be prevented or restrained, so that the stylet punctures the skin without fail.

Further, in the indwelling needle assembly of the present invention, preferably, the movement suppressing means is composed of an engaging part, which is provided on the outside surface of the stylet, and which engages with an edge part of the hole or the slit in an inserted condition.

This ensures that, when a puncturing operation is carried out, a tip-side edge part of the slit (or hole) and the engaging part engage with each other. Therefore, a problem wherein the stylet is pushed by the skin and retracted into the outer needle before the skin is punctured can be prevented or restrained, so that the stylet punctures the skin assuredly.

In addition, in the indwelling needle assembly of the present invention, preferably, the movement suppressing means comprises a blockage disposed between the outside surface of the stylet and the inside surface of the hole or slit in the seal member.

This ensures that a problem wherein the stylet is pushed by the skin and retracted into the outer needle before the skin is punctured can be prevented or restrained, so that the stylet punctures the skin securely.

Besides, the indwelling needle assembly of the present invention, preferably, further includes a compression member for compressing the seal member to close the hole or slit.

This increases friction between the outside surface of the stylet and the inside surface of the hole (or slit), wherein a problem in which the stylet is pushed by the skin and retracted into the outer needle before the skin is punctured can be prevented or restrained, so that the stylet can puncture the skin without fail.

In addition, preferably, the indwelling needle assembly of the present invention further includes a protector for covering at least the needlepoint of the stylet when the stylet is extracted from the outer needle.

This enhances safety by preventing accidents wherein, at the time the stylet is discarded after use, or at similar times, a worker or the like erroneously punctures his or her finger with the needlepoint.

Further, in the indwelling needle assembly of the present invention, preferably, a central axis of the outer needle and a central axis of the tube at the tip part thereof are substantially parallel with each other, in a condition in which the stylet is inserted into the outer needle.

This ensures that the tube will not pose an obstacle when puncturing is carried out by the outer needle and the stylet, such that the indwelling needle assembly is excellent in operability.

In addition, in the indwelling needle assembly of the present invention, preferably, the tube is composed mainly of polybutadiene.

This ensures that the tube has appropriate flexibility and chemical resistance, with excellent properties for preventing adsorption of chemicals thereon.

Also, in the indwelling needle assembly of the present invention, preferably, the varied outer diameter part comprises an enlarged diameter part, wherein the outer diameter of the stylet is enlarged.

This results in an increase in frictional resistance between the outside surface of the stylet and the inside surface of the slit (or hole) at the time a puncturing operation is performed. Therefore, a problem in which the stylet is pushed by the skin and retracted into the outer needle before the skin is punctured can be prevented or restrained, so that the stylet punctures the skin reliably. In other words, the indwelling needle assembly is excellent in operability when the puncturing operation is carried out.

In addition, in the indwelling needle assembly of the present invention, preferably, the varied outer diameter part is a reduced diameter part, wherein the outer diameter of the stylet is reduced.

This leads to an increase in frictional resistance between the outside surface of the stylet and the inside surface of the slit (or hole) when a puncturing operation is carried out. Therefore, a problem wherein the stylet is pushed by the skin and retracted into the outer needle before the skin is punctured is prevented or restrained, so that the stylet punctures the skin reliably. In other words, the indwelling needle assembly is excellent in operability at the time the puncturing operation is performed.

Also, in the indwelling needle assembly of the present invention, preferably, the slit is in the form of a straight line segment.

This permits the slit, in a closed state, to be easily placed in an opened state, so that the stylet can smoothly be passed through the slit.

In addition, in the indwelling needle assembly of the present invention, preferably, at least a portion of the stylet is solid.

This ensures that when the stylet is discarded, after operation thereof is completed, there is no danger of blood possibly remaining inside the stylet or of flowing out, thereby ensuring high safety.

Further, in the indwelling needle assembly of the present invention, preferably, the stylet is provided at least on a tip part of the stylet with a groove along the longitudinal direction thereof.

This ensures that, in a condition in which the stylet is inserted into the outer needle, the groove functions as a conduit for blood when the blood vessel is punctured. As a result, flashback of the blood can be reliably confirmed.

In addition, in the indwelling needle assembly of the present invention, preferably, the stylet is composed of a metallic material.

This enhances slidability of the stylet on the seal member. Specifically, frictional resistance between the seal member and the stylet can be reduced more reliably. As a result, the outer needle moves more smoothly, that is, the indwelling needle assembly exhibits better operability when a puncturing operation is performed.

Moreover, preferably, the indwelling needle assembly of the present invention further includes a slip-off preventive means for preventing the protector covering the needlepoint from slipping off from the needlepoint.

This makes it possible to securely maintain a condition in which the protector covers the needlepoint. Therefore, when the stylet is discarded, or at similar times, an accident in which a worker erroneously punctures his or her finger with the needlepoint can be reliably prevented, thereby ensuring high safety.

In addition, in the indwelling needle assembly of the present invention, preferably, the slip-off preventive means is composed of a connection member for connecting the protector and the stylet hub to each other.

This makes it possible to securely maintain a condition in which the protector covers the needlepoint. Therefore, when the stylet is discarded, or at similar times, an accident in which a worker erroneously punctures his or her finger with the needlepoint can be reliably prevented, thereby ensuring high safety.

Further, in the indwelling needle assembly of the present invention, preferably, the connection member can be extended and contracted, such that the connection member is contracted in a condition when the stylet is inserted into the outer needle, and the connection member is extended when the stylet is evulsed from the outer needle.

This ensures that the connection member does not obstruct the puncturing operation, so that the indwelling needle assembly has enhanced operability.

In addition, in the indwelling needle assembly of the present invention, preferably, the stylet penetrates into the connection member.

This ensures that the stylet functions as a guide for the connection member when the connection member is extended or contracted.

BEST MODE FOR CARRYING OUT THE INVENTION

Now, the indwelling needle assembly according to the present invention will be described in greater detail below, based on preferred embodiments of the invention as shown in the accompanying drawings.

First Embodiment

Figure 1:
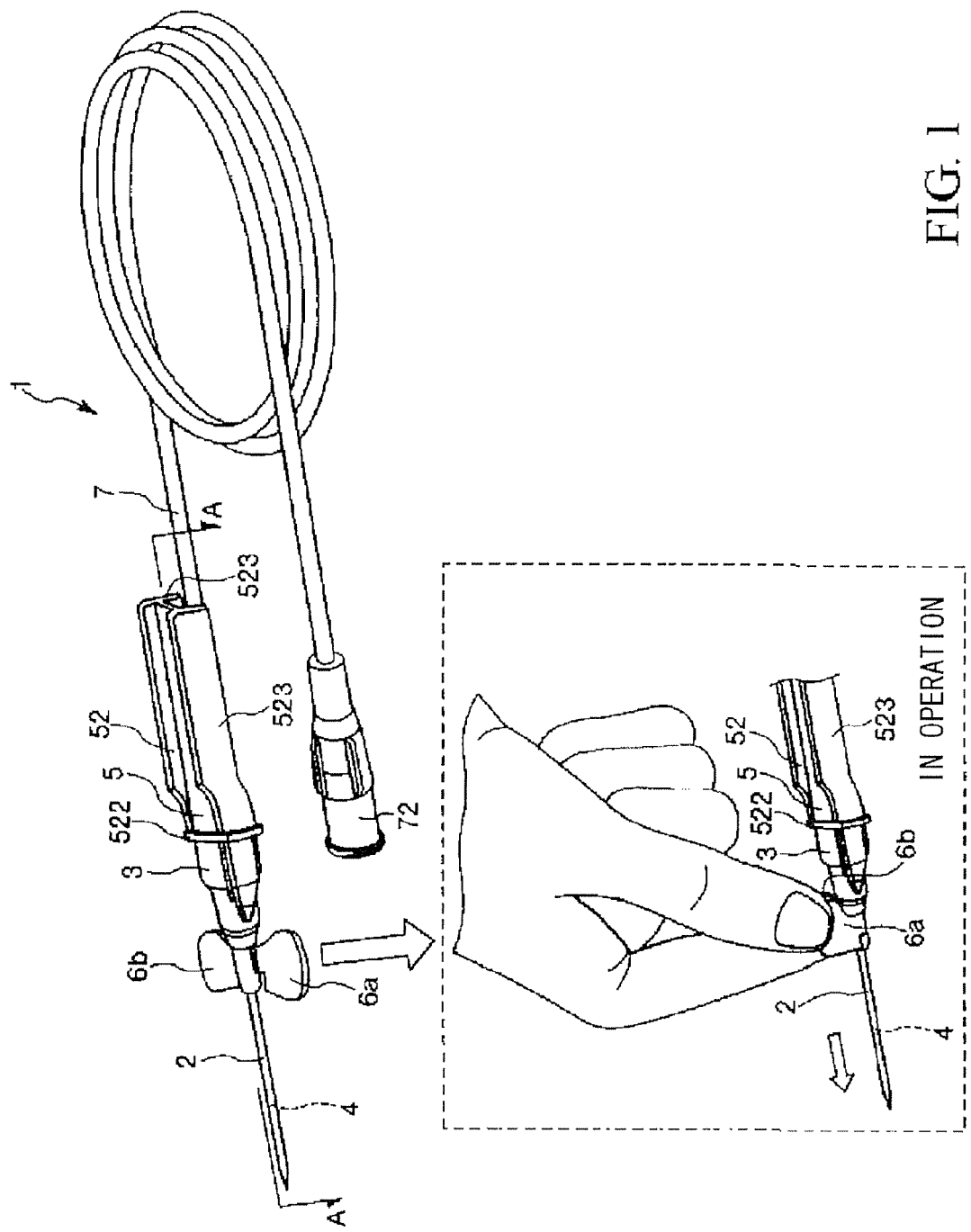
FIG. 1 is a perspective view of a first embodiment of the indwelling needle assembly according to the present invention.
Figure 2:
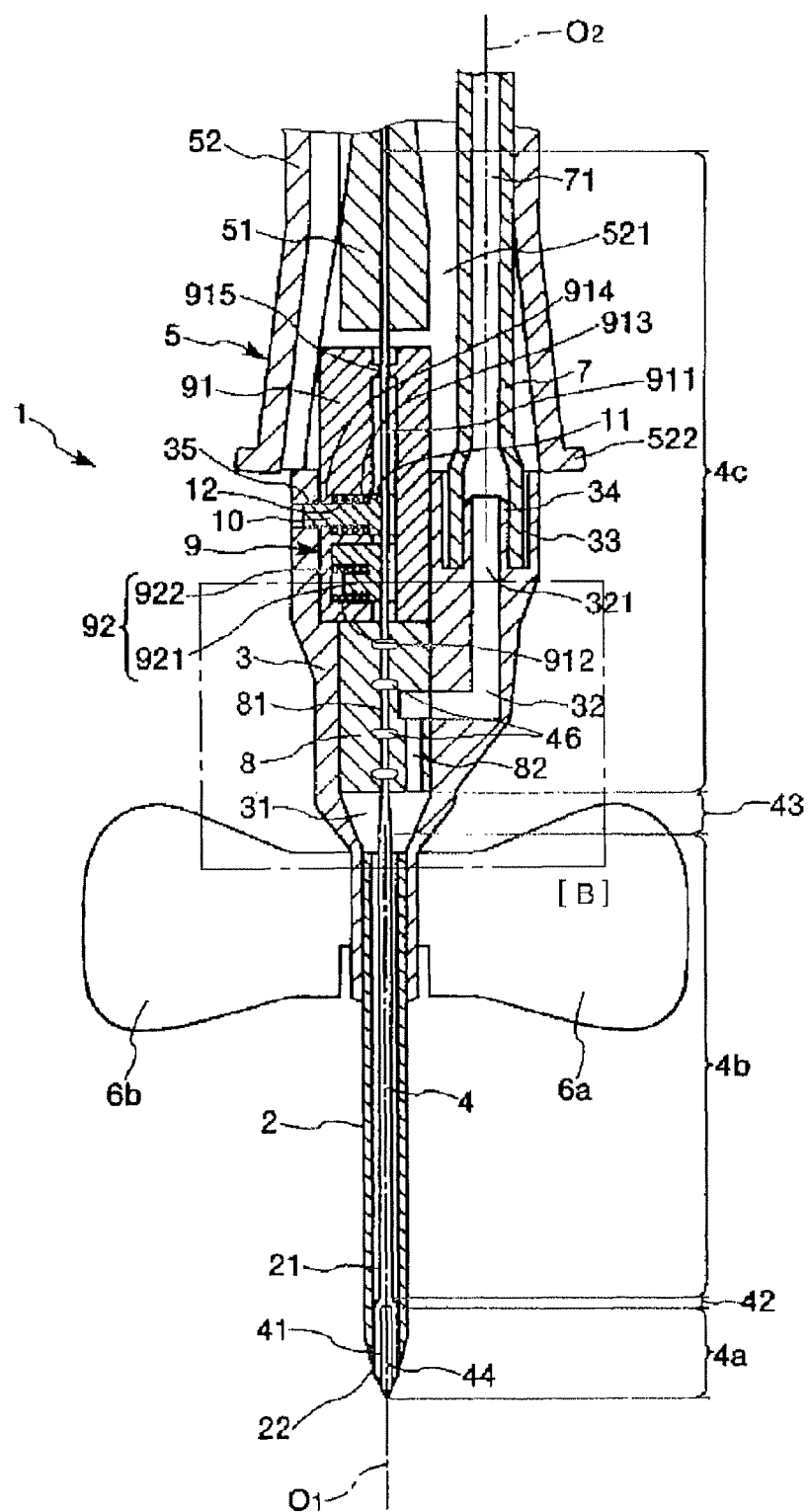
FIG. 2 is a sectional view taken along line A-A of FIG. 1.
Figure 3:
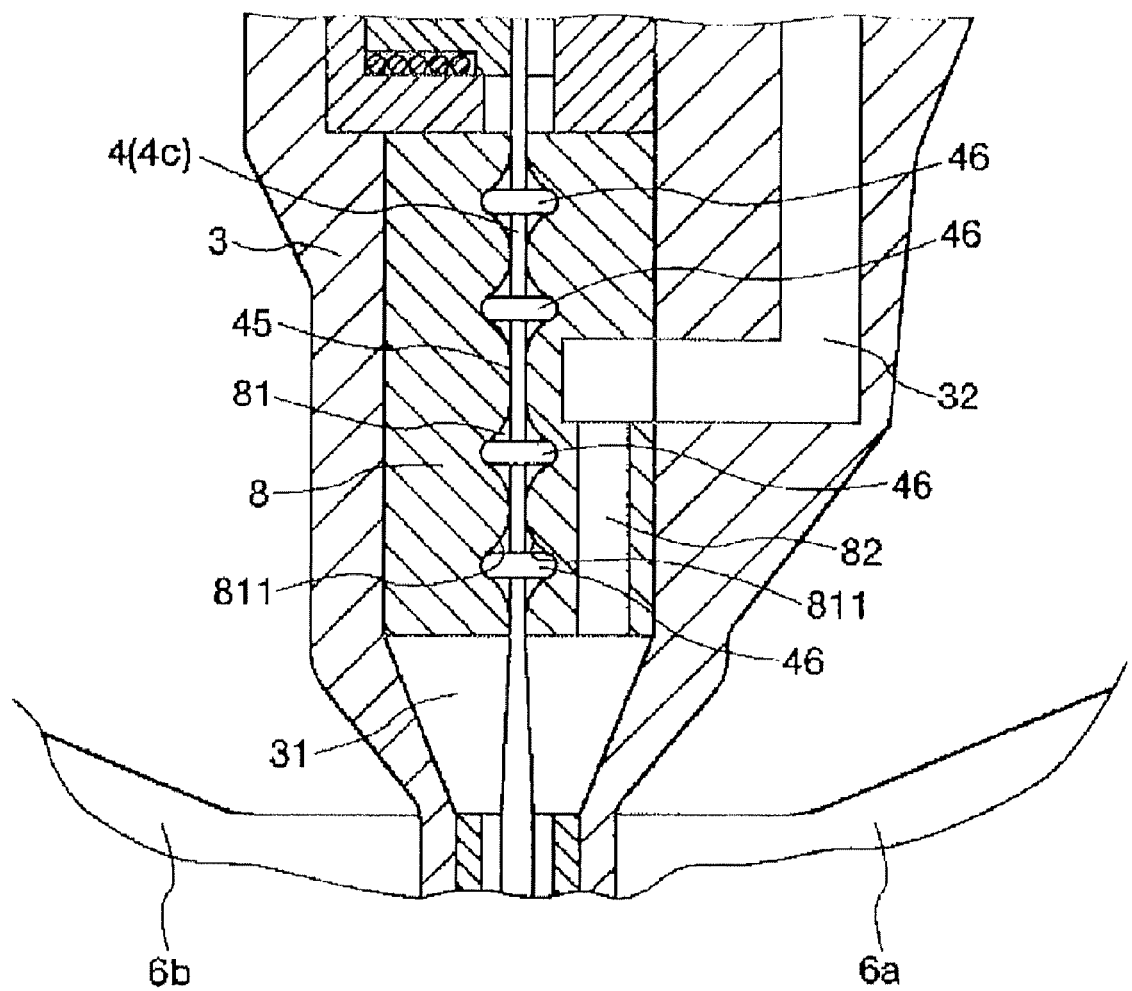
FIG. 3 is an enlarged view of a region [B] shown in FIG. 2.
Figure 4:
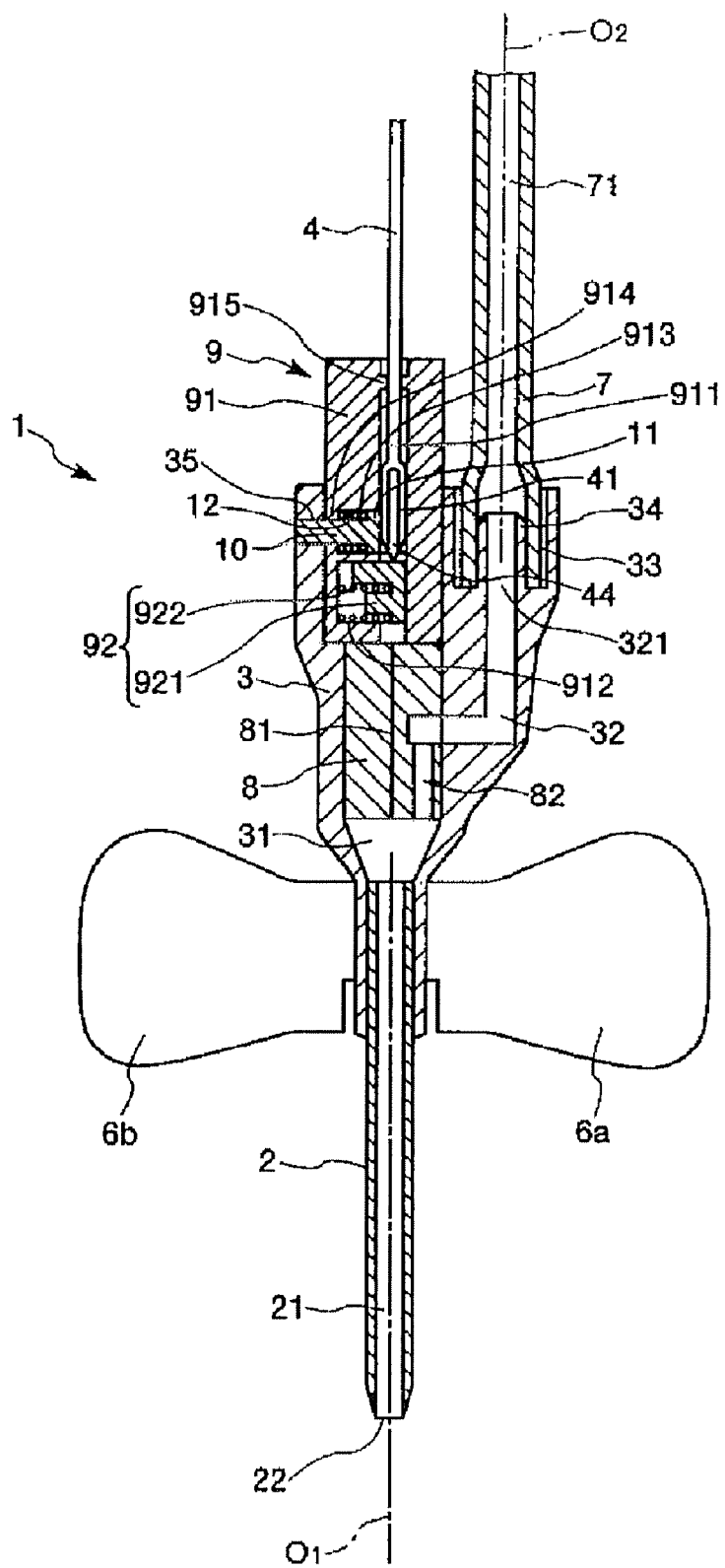
FIG. 4 is a sectional view taken along line A-A of FIG. 1.
Figure 5:
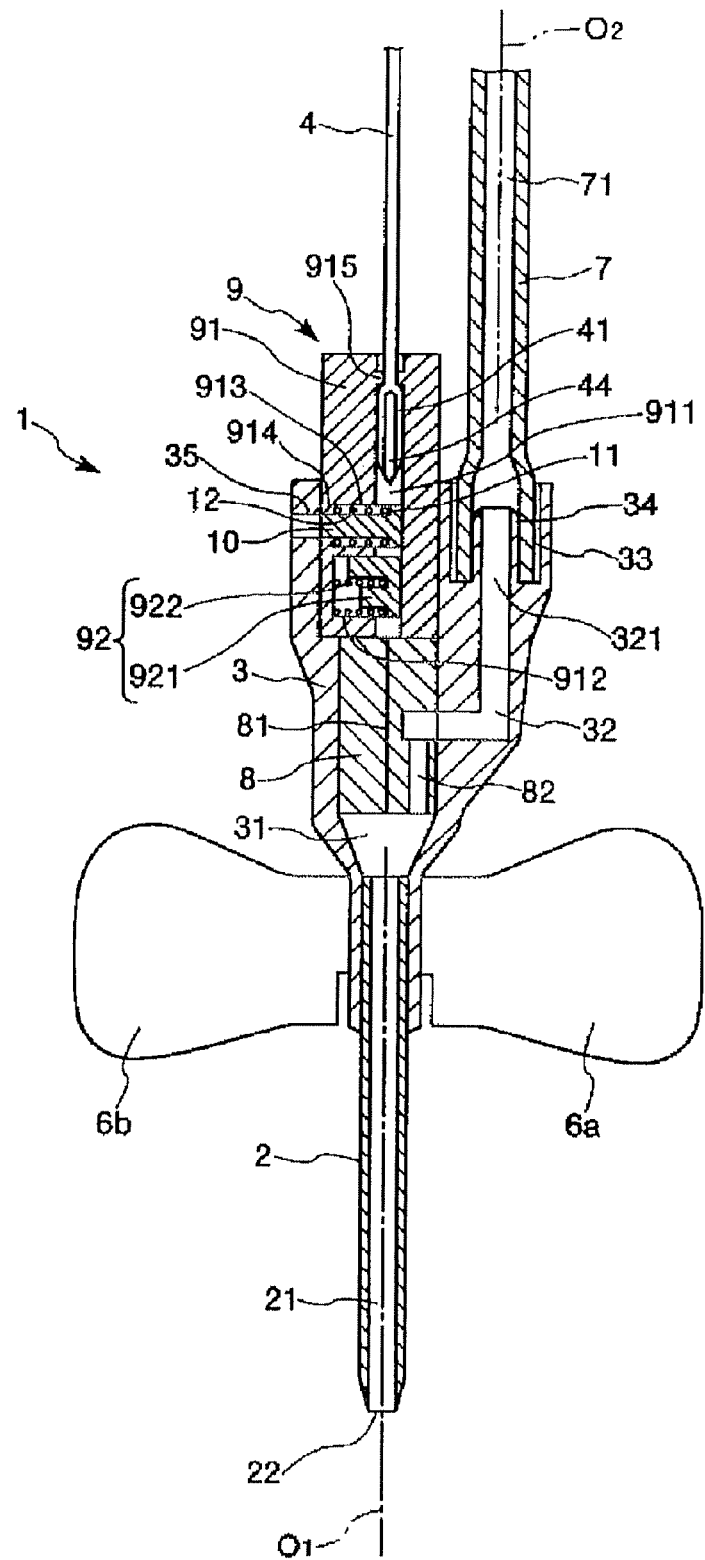
FIG. 5 is a sectional view taken along line A-A of FIG. 1.
Figure 6:
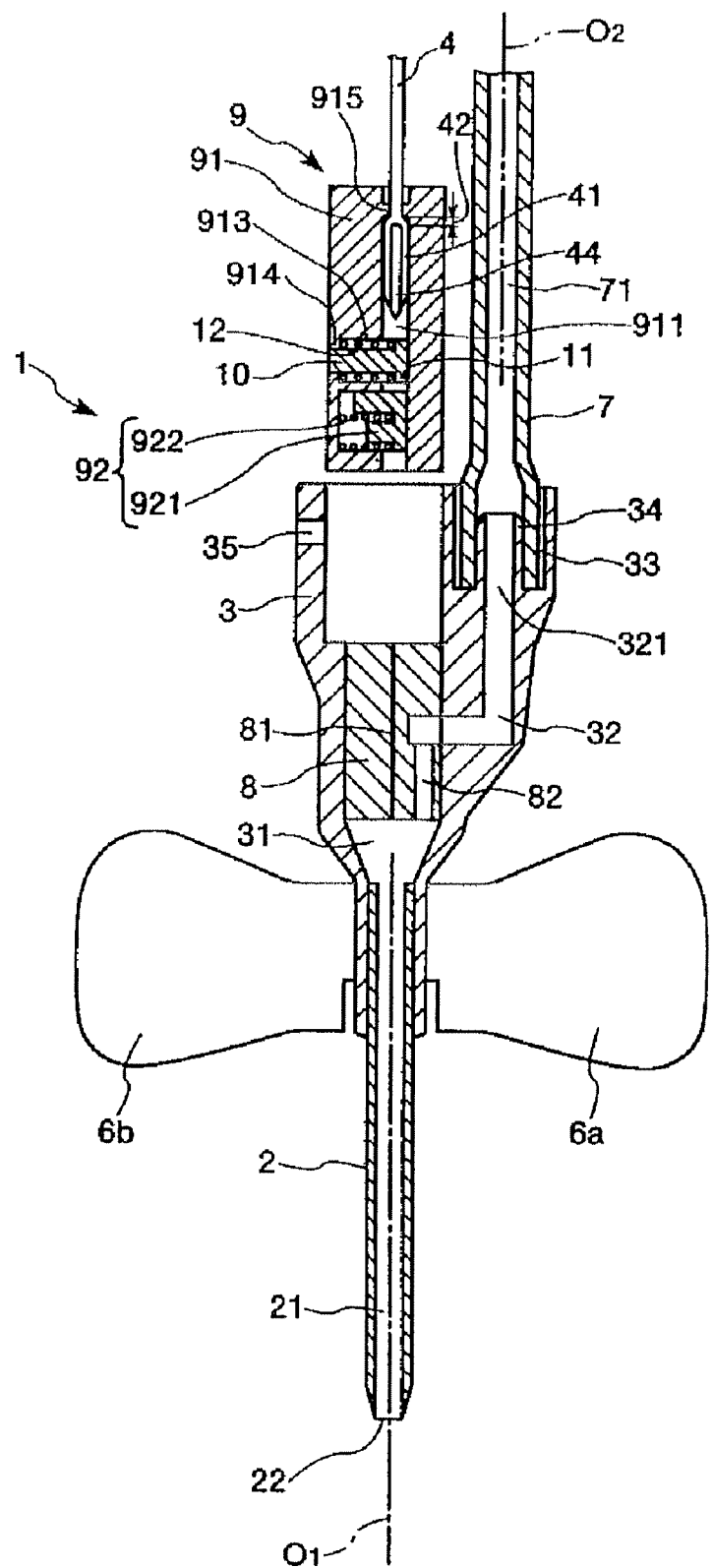
FIG. 6 is a sectional view taken along line A-A of FIG. 1.
Figure 7:
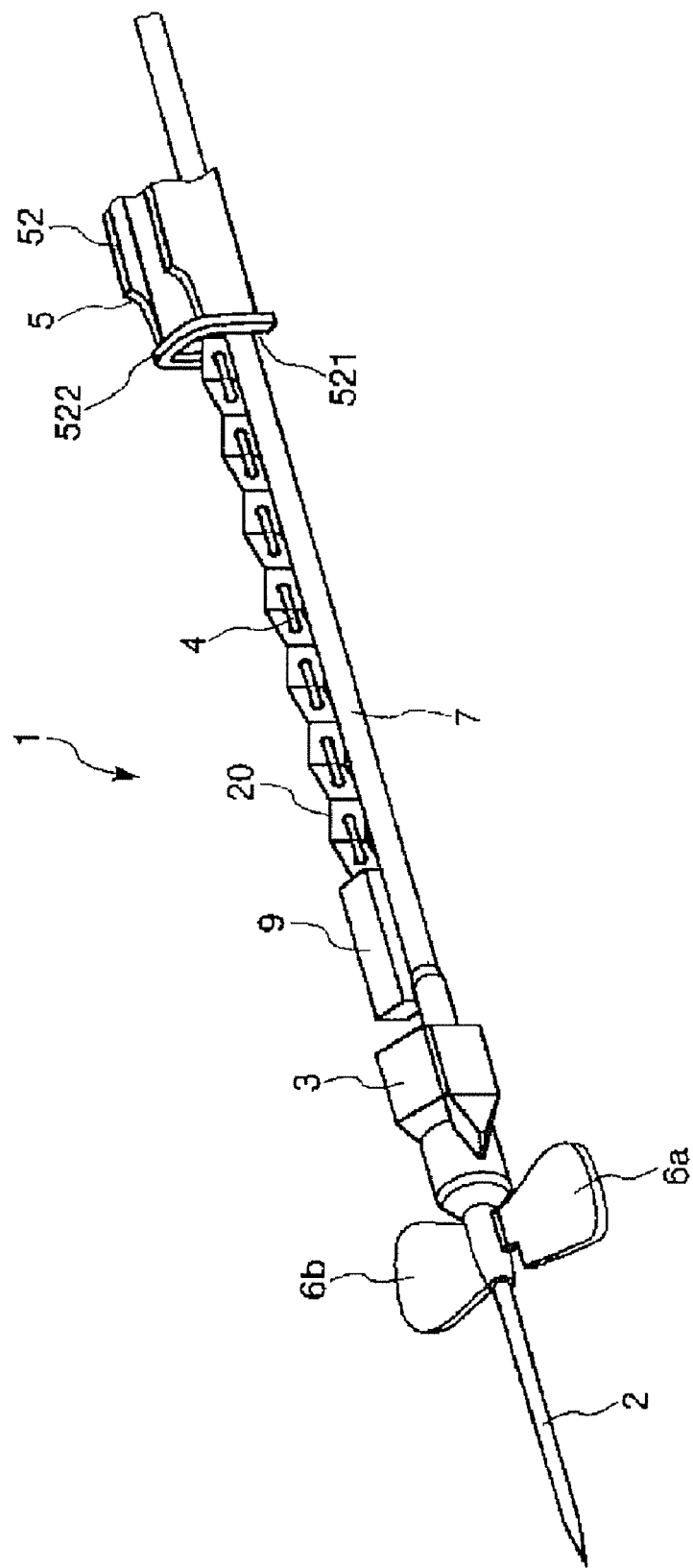
FIG. 7 is a perspective view, corresponding to FIG. 6, of the indwelling needle assembly shown in FIG. 1.
Figure 8:
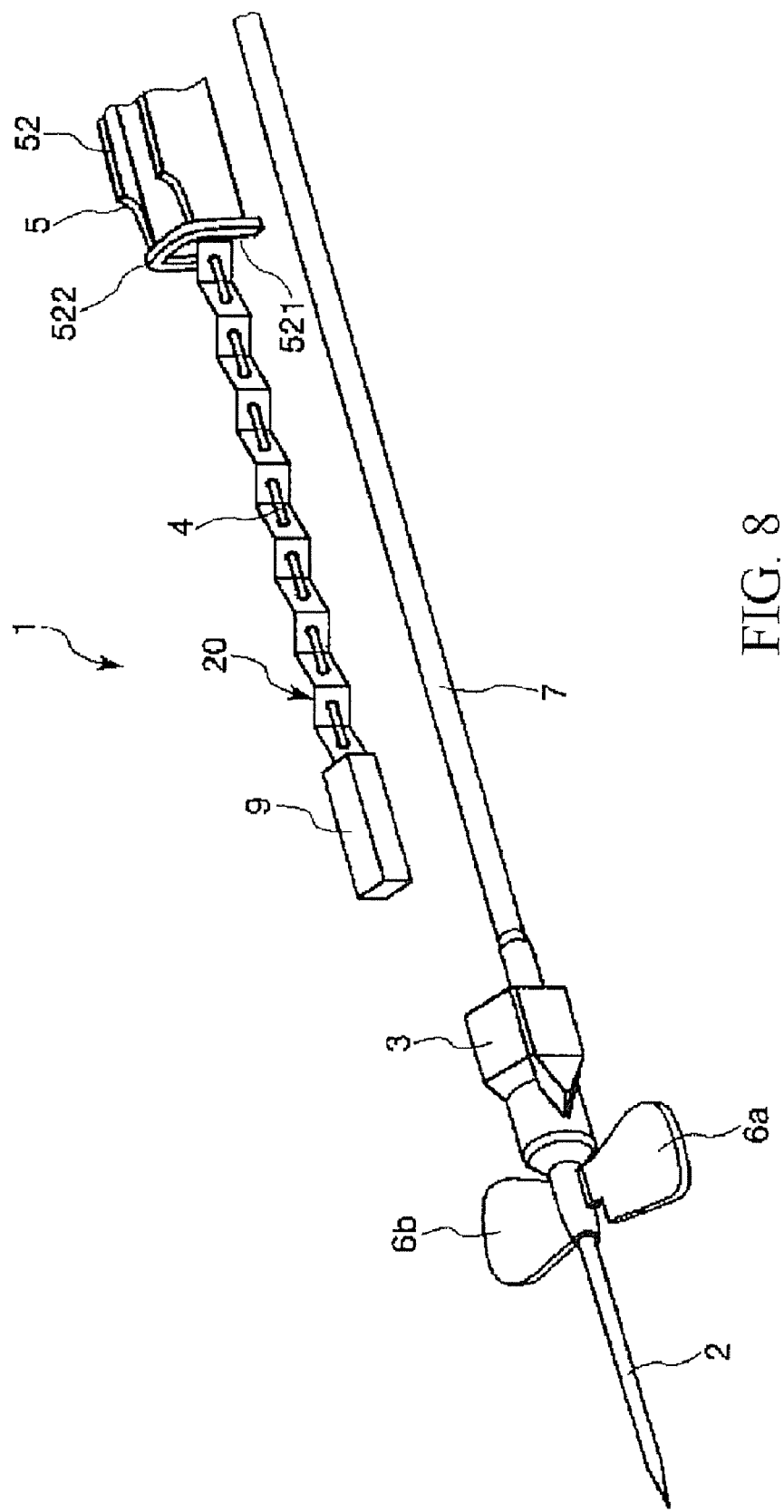
FIG. 8 is a perspective view showing a condition in which, in the indwelling needle assembly shown in FIG. 1, a tube is detached from a stylet hub.
Figure 14:
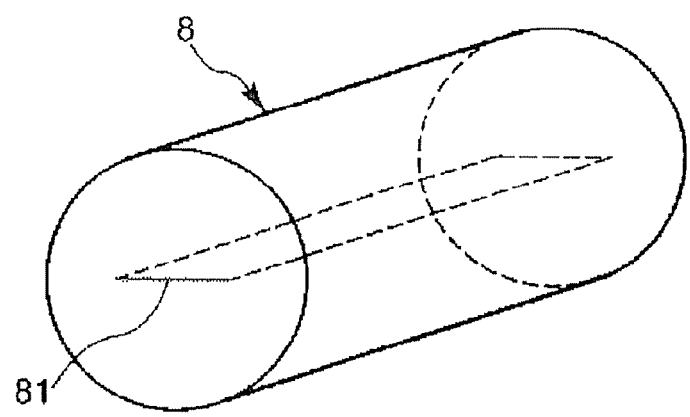
FIG. 14 is a perspective view showing a seal member possessed by the indwelling needle assembly shown in FIG. 1.

FIG. 1 is a perspective view of a first embodiment of the indwelling needle assembly according to the present invention; FIG. 2 is a sectional view taken along line A-A of FIG. 1; FIG. 3 is an enlarged view of a region [B] shown in FIG. 2; FIGS. 4 to 6 are sectional views taken along line A-A of FIG. 1; FIG. 7 is a perspective view, corresponding to FIG. 6, of the indwelling needle assembly shown in FIG. 1; FIG. 8 is a perspective view showing a condition in which, in the indwelling needle assembly shown in FIG. 1, a tube is detached from a stylet hub; and FIG. 14 is a perspective view of a seal member possessed by the indwelling needle assembly shown in FIG. 1.

Incidentally, in the following descriptions, the righthand side in FIGS. 1, 7 and 8 will be referred to as "the base", and the lefthand side as "the tip". Additionally, the upper side in FIGS. 2 to 6 will be referred to as "the base", and the lower side as "the tip". In addition, in FIG. 2 and in FIGS. 4 to 6, the slip-off preventive means, which is possessed by the indwelling needle assembly according to the present invention, is omitted from illustration.

The indwelling needle assembly 1 shown in the figures includes a hollow outer needle 2, an outer needle hub 3 secured to a base end part of the outer needle 2, a stylet 4 inserted into the outer needle 2, a stylet hub 5 secured onto a base end part of the stylet 4, and a tube 7 connected to a base end part (or side part) of the outer needle hub 3 so that the inner cavity 71 of the tube 7 communicates with the inner cavity 21 of the outer needle 2. Configurations of these components and sections shall be described below.

As the outer needle 2, a needle having a certain degree of flexibility preferably is used. The material constituting the outer needle 2 is preferably a resin material, particularly a soft resin material. Specific examples of such materials include fluoro-resins such as PTFE, ETFE, PFA, etc., olefin resins such as polyethylene, polypropylene, etc., and mixtures thereof, polyurethane, polyester, polyamide, polyether nylon resins, and mixtures of the olefin resin with an ethylene-vinyl acetate copolymer, etc.

A whole part or a part of the aforementioned outer needle 2 may have a property such that the interior thereof can be visually confirmed. In addition, the material constituting the outer needle 2 may be admixed with a radiopaque agent, such as barium sulfate, barium carbonate, bismuth carbonate, tungstic acid, etc., to obtain a contrast-enhancing property.

The outer needle hub 3 is secured (fixed) in a liquid-tight manner to a base end part of the outer needle 2 by a method such as caulking, fusing (heat fusing, high-frequency fusing, or the like), adhesion with an adhesive, etc.

The outer needle hub 3 is composed of a substantially tubular member, and the inside 31 thereof communicates with the inner cavity 21 of the outer needle 2.

A wall part on the righthand side in FIG. 2 (as well as in FIGS. 3 to 6) of the outer needle hub 3 is provided therein with a conduit 32, which opens at one end thereof into the inside 31 of the outer needle hub 3. The conduit 32 is substantially L-shaped, and the other end thereof opens into a recessed part 33 formed in the base of the outer needle hub 3, thereby forming an opening 321. In addition, at the tip face (bottom face) of the recessed part 33, a projecting part (connecting part) 34 having an annular shape surrounding the opening 321 is formed so as to project toward the base direction. This ensures that a liquid, such as a liquid drug, can be supplied into the outer needle 2 (outer needle hub 3) through the tube 7.

The projecting part 34 is inserted into the inner cavity 71 of a tip part of the tube 7, and one end part (tip part) of the tube 7 is connected to the outer needle hub 3.

In addition, on the left and right sides of the outer needle hub 3 as shown in FIG. 2 (also in FIGS. 3 to 6), a pair of vanes 6a and 6b are formed integrally with the outer needle hub 3. The vanes 6a and 6b are flexible, and are configured such that the vanes 6a, 6b can be opened and closed through bending or curving, in the vicinity of joint parts between the vanes 6a, 6b and the outer needle hub 3.

When the outer needle 2 and the stylet 4 are made to puncture a blood vessel or the like, the vanes 6a and 6b are pinched with the fingers to bring them into a closed condition, thereby enabling movement of the stylet 4 and the outer needle 2 along the longitudinal direction, i.e., a puncturing operation can be conducted (see FIG. 1). When the outer needle 2 is made to indwell, the vanes 6a and 6b are placed in an opened condition, and the vanes 6a and 6b are fixed to the skin with a pressure sensitive adhesive tape or the like.

The stylet 4, having a sharp needlepoint 41 at the tip thereof, is inserted into the outer needle 2. The indwelling needle assembly 1 is used in a condition where the stylet 4 is inserted into the outer needle 2, and the stylet hub 5 (described later) and the outer needle hub 3 are in contact with each other, i.e., in the condition shown in FIGS. 1 and 2. Hereinafter, this condition shall be referred to as "the assembled condition".

The length of the stylet 4 is set to a level such that, in the assembled condition, at least the needlepoint 41 thereof protrudes from the tip opening 22 of the outer needle 2.

The stylet 4 may be a hollow needle, but preferably is a solid needle. Where the stylet 4 is a solid needle, sufficient strength can be secured, while the outer diameter thereof may be small. Additionally, when the stylet 4 is solid, the danger of blood remaining inside the stylet 4 or of flowing-out therefrom, when the stylet 4 is discarded after completion of a procedure, can be prevented. Thus, high safety is ensured.

Incidentally, in the case that the stylet 4 is a hollow needle, blood flows into the hollow section of the stylet 4 when the stylet 4 punctures the blood vessel, whereby flashback of the blood is confirmed. When the stylet 4 is solid, on the other hand, blood flows into a gap between the stylet 4 and the outer needle 2, whereby flashback of the blood can be confirmed more swiftly.

Incidentally, the stylet 4 can be made with a configuration including both a hollow section and a solid section (e.g., a configuration wherein part of the inner cavity of a hollow needle is filled to obtain a hollow section on the tip side and a solid section on the base side). However, when the entire body of the stylet 4 is composed of a single member, the stylet 4 can be made at a reduced cost.

In addition, the stylet 4 has a plurality of sections (three, in the present embodiment), which differ in outer diameter. Specifically, the stylet 4 has a maximum outer diameter section 4a on the tip side (tip part), a minimum outer diameter section 4c on the base side, and an intermediate outer diameter section 4b between the maximum outer diameter section 4a and the minimum outer diameter section 4c.

Further, the stylet 4 includes a first varied outer diameter section 42 (which continuously varies in outer diameter) at a boundary between the maximum outer diameter section 4a and the intermediate outer diameter section 4b, and a second varied outer diameter section 43 (which continuously varies in outer diameter) between the intermediate outer diameter section 4b and the minimum outer diameter section 4c.

At each of the varied outer diameter sections 42 and 43, the outer diameter of the stylet 4 may be varied stepwise. However, when the stylet 4 varies continuously in its outer diameter (i.e., is tapered), each of the varied outer diameter sections 42 and 43 can be prevented from becoming caught on a tip edge part of the slit 81 in the seal member 8 (described later), or on a tip edge part of a stylet passage 911 within a protector body 91, or the like, when the stylet 4 is evulsed from the outer needle 2. Therefore, an operation to evulse the stylet 4 from the outer needle 2 can be carried out more smoothly and assuredly.

Incidentally, the varied outer diameter sections 42 and 43 may be formed when the stylet 4 is produced. Alternatively, a step or steps inevitably formed at the time of forming a groove 44 (described later) may be utilized.

In addition, the maximum outer diameter section 2a has an outer diameter set approximately equal to the inner diameter of the outer needle 2, so that the outer diameter section 2a makes close contact with the inside surface of the outer needle 2, in a condition in which the stylet 4 is inserted into the outer needle 2. An outer peripheral part of the maximum outer diameter section 4a is provided with the groove (conduit) 44 therein, in a recessed form along the longitudinal direction of the stylet 4. The groove 44 provides communication between the tip opening 22 of the outer needle 2 and the inside 31 of the stylet hub 3, in a condition in which the stylet 4 is inserted into the outer needle 2. The groove 44 functions as a blood (body fluid) conduit, at the time of puncturing a blood vessel, for example. This makes it possible to securely confirm flashback of the blood.

Examples of the materials constituting the aforementioned stylet 4 include metallic materials, such as stainless steel, aluminum, aluminum alloys, titanium, and titanium alloys, etc.

The stylet hub 5 is secured (fixed) to a base end part of the stylet 4. The stylet hub 5 is composed of a fixing section 51 for fixing the stylet 4, and a cover section 52 provided on the outer peripheral side of the fixing section 51. Preferably, the fixing section 51 and the cover section 52 are formed integrally.

In addition, in an assembled condition, the tube 7 is disposed between the fixing section 51 and the cover section 52. Namely, in the assembled condition, the tube 7 is inserted into the stylet hub 5. This ensures that the tube 7 can be prevented from obstructing operation of the indwelling needle assembly 1.

In addition, the cover section 52 is provided with a pair of guides 523, 523 for guiding the tube 7 (see FIG. 1). The guides 523 constitute side walls (side parts) of the cover section 52, and guide the tube 7 such that a center axis $O_2$ of the tube 7 at the tip part thereof will remain substantially parallel to the longitudinal direction of the stylet hub 5 (the center axis $O_1$ of the outer needle 2).

In addition, when the stylet 4 is evulsed from the outer needle 2, the tube 7 can be detached from the stylet hub 5 through a clearance (gap 521) provided between both of the guides 523.

The fixation of the stylet 4 to the stylet hub 5 (the fixing section 51) may be carried out by a method such as fitting, caulking, fusing, adhesion with an adhesive, etc., or by any combination of these methods. Further, in the event that the stylet 4 is hollow, it is necessary, for example, to provide a seal, such that blood flowing back upon puncturing the blood vessel with the stylet 4 will not run out through the base of the stylet 4.

In addition, as shown in FIG. 1 (as well as in FIGS. 2, 7 and 8), a flange 522 may be provided on the outer periphery of the tip of the stylet 5. By providing the flange 522, for example, when the stylet 4 is evulsed from the outer needle 2, the fingers may be placed on the flange 522 to thereby facilitate performance of the evulsing operation, and thus the operation can be carried out more easily and assuredly.

The stylet hub 5 and the above-described outer needle hub 3 are preferably formed from a transparent (colorless transparent), colored transparent, or semi-transparent resin, thereby ensuring a property in which the inside can be visually confirmed. This ensures that, when the outer needle 2 has accessed a blood vessel, flashback of the blood flowing in through the groove 44 of the stylet 4, as previously mentioned, can be visually confirmed. In addition, when the stylet 4 is solid, all of the flashbacked blood under the pressure inside the blood vessel, for example, flows back through the groove 44, which enhances the visual confirmation thereof.

The materials constituting the outer needle hub 3, the stylet hub 5, and the vanes 6a and 6b are not particularly limited. Examples of such materials include various resin materials made up of polyolefins, such as polyethylene, polypropylene, ethylene-vinyl acetate copolymer, etc., polyurethane, polyamides, polyesters, polycarbonate, polybutadiene, polyvinyl chloride, etc.

The tube 7 is flexible and, as mentioned above, one end of the tube 7 is connected to the base end part of the outer needle hub 3. A connector 72 is mounted on the other end section (base end part) of the tube 7. A connector mounted at an end of an infusion line for supplying an infusion liquid (liquid medicine) to be dosed, or a mouth (tip part) of a syringe in which a liquid medicine is contained, may be connected to the connector 72.

Incidentally, the material constituting the tube 7 is not particularly limited. Examples of such materials include polyolefins, such as polyethylene, polypropylene, ethylene-vinyl acetate copolymer, etc., polyvinyl chloride, polybutadiene, polyamides, polyesters, etc., among which polybutadiene is particularly preferred. In the case that the tube 7 is formed from polybutadiene, the tube 7 has appropriate flexibility and chemical resistance, together with the excellent property of preventing adsorption of medicines thereon.

Further, the indwelling needle assembly 1 includes a cylindrical (block-like) seal member 8 at the inside 31 of the outer needle hub 3 (see FIG. 14). The seal member 8 has a slit 81 provided substantially in the center thereof, which penetrates through the seal member 8 along the longitudinal direction thereof. Herein, the term "slit" implies a slit which normally is closed in its natural condition. The term "natural condition" implies a condition in which no external forces are exerted on the seal member 8.

As shown in FIG. 14, the slit 81 is in the shape of a straight line segment.

In addition, as shown in FIGS. 2 and 3, in an assembled condition, the minimum outer diameter section 4c of the stylet 4 is located within the slit 81. Such a configuration prevents the seal member 8 (slit 81) from undergoing a permanent or semi-permanent deformation, which, if occurred, would lower the sealing performance thereof.

Examples of materials constituting the seal member 8 include various elastic materials, such as various rubber materials (particularly vulcanized rubbers) such as natural rubber, isoprene rubber, butyl rubber, butadiene rubber, styrene-butadiene rubber, urethane rubber, nitrile rubber, acrylic rubber, fluoro-rubber, silicone rubber, etc., various thermoplastic elastomers based on urethane, polyester, polyamide, olefin, styrene, etc., and mixtures thereof.

In addition, the seal member 8 is provided with a conduit 82 therein, at a location different from that of the slit 81. The conduit 82 opens at the tip face and at a side surface of the seal member 8. The conduit 82 is roughly L-shaped.

When the seal member 8 is inserted into the outer needle hub 3, an opening where the conduit 82 opens at the side surface of the seal member 8, and an opening where the above-mentioned conduit 32 opens toward the inside 31 of the outer needle hub 3, are set to coincide with each other, and a crank-shaped junction conduit is formed (completed) thereby. The junction conduit enables communication between the inner cavity 21 of the outer needle 2 and the inner cavity 71 of the tube 7. Such a configuration makes it possible for the junction conduit to be comparatively short, and thereby prevents the outer needle hub 3 from becoming enlarged in size.

The indwelling needle assembly 1 also is provided with a movement suppressing means for inhibiting or suppressing movement of the stylet 4 relative to the seal member 8, when the vanes 6a and 6b are operated in an assembled condition (i.e., the inserted condition in which the stylet 4 is inserted into the outer needle 2) (see FIG. 1).

The movement suppressing means in the present embodiment is composed of enlarged diameter parts (varied outer diameter parts) 46, where the outer diameter of the minimum outer diameter section 4c of the stylet 4 is enlarged (see FIGS. 2 and 3). Such enlarged diameter parts 46 are made up of circular disk-like parts, which are provided on the outside surface 45 of the minimum outer diameter section 4c of the stylet 4, so that the outer diameter of the minimum outer diameter section 4c (stylet 4) varies (increases) abruptly. In addition, the edge parts of the enlarged diameter parts 46 are rounded.

Further, the indwelling needle assembly 1 is provided with four enlarged diameter parts 46, disposed at intervals along the longitudinal direction of the stylet 4.

By providing such enlarged diameter parts 46, the area of contact between the stylet 4 (the outside surface 45 thereof, inclusive of the enlarged diameter parts 46) and the inside surface 811 of the slit 81 is enlarged, compared to the case in which the enlarged diameter parts 46 are not provided. As a result, when a puncturing operation is conducted by pinching the vanes 6a and 6b with the fingertips in an assembled condition of the indwelling needle assembly 1, frictional resistance between the outside surface 45 of the stylet 4 and the inside surface 811 of the slit 81 increases. Therefore, a problem wherein the stylet 4 is pushed by the skin and retracted into the outer needle 2 before the skin has been punctured is prevented or restrained, so that the stylet 4 can puncture the skin assuredly. In other words, the indwelling needle assembly 1 exhibits excellent operability upon performing a puncturing operation.

Incidentally, each of the enlarged diameter parts 46 may be formed integrally with the stylet 4. Alternatively, the enlarged diameter parts 46 may be prepared separately from the stylet 4 and then disposed (provided) on the stylet 4 by securing (for example, by welding) the separate components (enlarged diameter parts 46) to the stylet 4. In addition, when the stylet 4 is formed from a metallic material as mentioned above, the enlarged diameter parts 46 can easily be provided on and secured to the stylet 4 by means of the above-mentioned forming method (disposing method).

Further, the number of formed (disposed) enlarged diameter parts 46 is not limited to four, but may be, for example, one, two, three, or five or more.

Furthermore, the indwelling needle assembly 1 has a protector 9 for protecting at least the needlepoint 41 of the stylet 4, when the stylet 4 is evulsed from the outer needle 2. Hereinafter, the protector 9 will be described.

As shown in FIG. 2 (as well as in FIGS. 4 to 6), the protector 9 includes a protector body 91 having a substantially rectangular parallelepiped outer shape, and a shutter means 92 disposed inside the protector body 91.

Substantially in the center of the protector body 91, a stylet passage 911, into which the stylet 4 is inserted, is formed that penetrates through the protector body 91 along the longitudinal direction thereof.

The stylet passage 911 is substantially circular in cross section, wherein the inner diameter thereof is equal to or slightly greater than the outer diameter of the maximum outer diameter section 4a of the stylet 4.

In addition, the inside wall (i.e., the surface fronting on the stylet passage 911) on the tip side of the protector body 91 is provided with a recessed part 912.

The shutter means 92 is stored inside the recessed part 912. The shutter means 92 is composed of a block-shaped shutter member 921, together with a coil spring (urging means) 922 for urging the shutter member 921 toward the side of the stylet passage 911.

The shutter means 92 can be displaced between a first posture (the posture shown in FIG. 2), in which the majority of the shutter means 92 is retracted into the recessed part 912 and the stylet 4 is capable of being inserted into the stylet passage 911, and a second posture (the posture shown in FIG. 4) in which a portion of the shutter member 921 enters into the stylet passage 911, thereby inhibiting the needlepoint 41 of the stylet 4 from passing therethrough.

With the above protector 9, after use, the needlepoint 41 of the stylet 4 can be covered speedily and safely by means of a simple operation. In addition, due to the action of the shutter means 92, once covered, the needlepoint 41 is prevented from protruding from the tip of the protector 9 (the protector body 91). Therefore, an accident in which the worker erroneously punctures his or her finger with the needlepoint 41 when discarding the stylet 4, or upon similar occasions, can be prevented. Thus, high safety is ensured.

Moreover, in the assembled condition, substantially the whole part of the protector 9 is covered both by the outer needle hub 3 and by the stylet hub 5. This ensures that the protector 9 does not obstruct the puncturing action with the outer needle 2 and the stylet 4, so that the puncturing operation can be performed more assuredly. Incidentally, the protector 9 may be covered, substantially in its entirety, with either one of the outer needle hub 3 or the stylet hub 5.

Furthermore, the protector 9 is configured so that, in the assembled condition, the protector 9 is located on the base side relative to the seal member 8. This eliminates the need to pass the protector 9 through the slit 81 in the seal member 8 when the stylet 4 is evulsed from the outer needle 2. Therefore, the evulsing operation can be performed more easily and securely. In addition, such a configuration makes it possible for the overall length of the stylet 4 to be shorter, whereby the size of parts, exclusive of the tube 7 of the indwelling needle assembly 1, can be reduced.

As shown in FIGS. 7 and 8, the indwelling needle assembly 1 has a connection member 20, which acts as a slip-off preventive means for preventing the protector 9 from slipping off of the needlepoint 41 when the protector 9 covers the needlepoint 41.

The connection member 20 is configured so as to connect the protector 9 and the stylet hub 5 to each other. This prevents the protector 9 from slipping off from the stylet hub 5 (needlepoint 41), so that a condition in which the protector 9 covers the needlepoint 41 can be maintained securely. Therefore, an accident, in which the worker erroneously punctures his or her finger with the needlepoint 41 when discarding the stylet 4, or on similar occasions, can be prevented. High safety thereby is ensured.

In addition, the connection member 20 has a bellows-like shape, and therefore can be extended and contracted as desired. The connection member 20 is contracted, or folded, in an assembled condition, and is extended, or unfolded, in a state in which the stylet 4 is evulsed from the outer needle 2 (i.e., the condition shown in FIGS. 7 and 8).

The above-described connection member 20 is contracted in the assembled condition, and is stored in a contracted state inside the stylet hub 5. This ensures that the connection member 20 does not act as an obstacle during the puncturing operation. Thus, operability of the indwelling needle assembly 1 is enhanced. In addition, a merit results in that the indwelling needle assembly 1 can be reduced in size.

Further, in a condition in which the connection member 20 is contracted, as well as in a condition in which the connection member 20 is extended, the stylet 4 penetrates through the connection member 20. Thus, when the connection member 20 is extended and contracted, the stylet 4 functions as a guide for the connection member 20. Therefore, it is possible to reliably prevent the connection member 20 from being contracted in an undesired manner, or from being contracted without being contained within the stylet hub 5, when the indwelling needle assembly 1 is placed in an assembled condition (i.e., when the indwelling needle assembly 1 is manufactured).

Moreover, the above indwelling needle assembly 1 includes a fixing means for securing the protector 9 to the outer needle hub 3, and an engaging means (movement restraining means) for restraining the stylet 4 from moving in relation to the protector 9 in a direction opposite to the needlepoint 41, by engagement between the stylet 4 and the protector 9, in a condition in which at least the needlepoint 41 of the stylet 4 is covered by the protector 9. The fixing means and the engaging means shall be described in detail below.

<Fixing Means>

First, the fixing means will be described.

The inside wall of the protector body 91 is provided with a through-hole 913 therein on the base side of the recessed part 912. A projecting part 914, which projects toward the inside, is formed at the left end of the through-hole 913, as shown in FIG. 2.

A fixing pin 10, having a flange part 11 on the righthand end thereof, as shown in FIG. 2, is inserted in the through-hole 913, under a condition in which a coil spring 12 is stored therein. In this condition, as shown in FIG. 2, the left end of the coil spring 12 is placed in contact with the projecting part 914, and the righthand end thereof is placed in contact with the flange part 11.

In addition, a through-hole 35 into which the fixing pin 10 can be inserted is formed in a base end part of the left side wall part of the outer needle hub 3, as shown in FIG. 2.

In the condition where the stylet 4 is inserted into (penetrates through) the stylet passage 911, the right surface of the fixing pin 10 is placed in contact with the outer peripheral surface (outside surface 45) of the stylet 4, and the left end part of the fixing pin 10 protrudes from the through-hole 913 and is inserted into the through-hole 35. Owing thereto, the protector 9 is fixed to the outer needle hub 3 (see FIGS. 2 and 4).

On the other hand, when the stylet 4 is evulsed from the stylet passage 911, the fixing pin 10 is pushed by the coil spring 12 so as to move toward the right side in FIG. 5, whereas the left end part of the fixing pin 10 comes out of the through-hole 35. As a result, fixation of the protector 9 with respect to the outer needle hub 3 is cleared (see FIG. 5).

Thus, in the present embodiment, the fixing means for fixing the protector 9 to the outer needle hub 3 is constituted mainly by the through-hole 913, the fixing pin 10, the coil spring 12, and the stylet 4.

Moreover, as shown in FIG. 4, in this embodiment, the fixing means operates after the shutter means 92 has been operated. More specifically, fixation of the protector 9 to the outer needle hub 3 by the fixing means is maintained during a condition in which the shutter means 92 has been operated. Such a configuration ensures that the shutter means 92 is operated assuredly, in a condition where fixation of the protector 9 to the outer needle hub 3 is cleared. Therefore, an accident in which the worker erroneously punctures his or her finger with the needlepoint 41 when discarding the stylet 4, or on similar occasions, can be prevented securely.

<Engaging Means>

The engaging means will be described below.

A base end part of the protector body 91 is provided with a reduced diameter part 915 where the stylet passage 911 is reduced in diameter. The inner diameter of the reduced diameter part 915 is greater than the outer diameters of both the intermediate outer diameter section 4b and the minimum outer diameter section 4c of the stylet 4, and is smaller than the outer diameter of the maximum outer diameter section 4a.

This ensures that, when the stylet 4 is evulsed from the outer needle 2, the minimum outer diameter section 4c, the second varied outer diameter section 43, and the intermediate outer diameter section 4b can all pass through the reduced diameter part 915. However, the first varied outer diameter section 42 cannot pass through the reduced diameter part 915, but rather becomes engaged with the reduced diameter part 915 (see FIG. 5).

In other words, in the present embodiment, the first varied outer diameter section 42 and the reduced diameter part 915 constitute the engaging means for engagement between the stylet 4 and the protector 9.

When such an engaging means is provided, in a series of operations for evulsing the stylet 4 from the outer needle 2, it is possible for the stylet 4 to become engaged with the protector 9, and to release the protector 9 from the outer needle hub 3 (see FIGS. 5 and 6), so that such operations can be readily carried out. In addition, the stylet 4 can be prevented from coming off from the protector 9 while the protector 9 is in a state of covering the needlepoint 41.

Further, since the first varied outer diameter section 42 and the reduced diameter part 915 are formed respectively on the stylet 4 and on the protector 9, the configuration is simple. Also, an increase in the number of component parts is prevented, which contributes to reductions in size and diameter.

In the above-described indwelling needle assembly 1, as shown in FIGS. 1 and 2, the center axis $O_1$ of the outer needle 2 and the center axis $O_2$ of the tube 7 at the tip part thereof are substantially parallel with each other in the assembled condition in which the tube 7 is connected to the base end part of the outer needle hub 3. In other words, the tube 7 protrudes in the base direction (proximal direction) from the base of the outer needle hub 3.

If the tube 7 were to project toward a lateral side of the outer needle hub 3, the outer needle hub 3 would be pulled sideways by the tube, i.e., in a direction in which the tube 7 projects from the outer needle hub 3, at the time puncturing is performed with the outer needle 2 and the stylet 4, resulting in a loss of good balance. In such a case, therefore, intended operations are difficult to carry out.

Further, if the tube 7 were to project toward the upper side of the outer needle hub 3, there is a possibility for the tube 7 to be heavily bent (kinked) when the outer needle hub 3 is fixed to the patient, at a time when the outer needle 2 is caused to indwell within the patient's blood vessel or the like.

Further, if the tube 7 were to project toward the lateral side or toward the upper side of the outer needle hub 3, it becomes necessary to grip the stylet hub 5 while avoiding the tube 7, so as not to pinch the tube 7, while moving only the outer needle 2 forward into the blood vessel after entry of the outer needle 2 into the blood vessel. Thus, the operation in this instance becomes quite troublesome.

On the other hand, in the indwelling needle assembly 1 according to the present invention, the tube 7 projects toward the base direction of the outer needle hub 3, and is covered with the stylet hub 5. Therefore, the above-mentioned inconveniences can be prevented from occurring, and excellent operability is ensured.

Next, an example of a method for using the indwelling needle assembly 1 (i.e., in the case of puncturing a blood vessel) shall be described in detail below.

[1] The indwelling needle assembly 1 is placed in the assembled condition, and a connector mounted on an end of an infusion line is preliminarily connected to the connector 72, so as to enable an infusion liquid to be supplied from the infusion line.

In this instance, a predetermined portion of the tube 7 or the infusion line is clamped, for example, by means of a clamp (an example of a conduit opening/closing means), thereby preliminarily closing the inner cavity.

[2] Next, closure of the tube 7 or the infusion line by the clamp or the like is cleared, and the infusion liquid from the infusion line is introduced through the tube 7 into the outer needle hub 3.

The infusion liquid introduced into the outer needle hub 3 fills the conduit 32, the conduit 82, and the space, on the tip side relative to the seal member 8, of the inside 31 of the outer needle hub 3, and the infusion liquid is introduced into the inner cavity 21 of the outer needle 2. This results in priming of the inner cavity 21 of the outer needle 2 with the infusion liquid. In this case, a portion of the infusion liquid flows out through the tip opening 22 of the outer needle 2.

[3] When priming has been completed as described above, the tube 7 or the infusion line is preliminarily closed again by the clamp or the like. The vanes 6a and 6b are closed by pinching with the fingers, and, with the vanes 6a and 6b serving as a gripping part (operating part), the outer needle 2 and the stylet 4 bound as one body are caused to puncture the patient's blood vessel (vein or artery). In this instance, as mentioned above, a large frictional resistance is generated between the outside surface 45 of the stylet 4 and the inside surface 811 of the slit 81, so that the problem whereby the stylet 4 is pushed by the skin and retracted into the outer needle 2 is prevented or restrained. Therefore, the stylet 4 and the outer needle 2, particularly the stylet 4, can puncture the blood vessel (skin) assuredly.

When the blood vessel is accessed by the outer needle 2, blood flows back toward the base direction inside the inner cavity of the outer needle 2, via the groove 44 of the stylet 4, due to the pressure inside the blood vessel (blood pressure). Therefore, backflow of blood can be confirmed at least at one part of the outer needle 2, the outer needle hub 3, the stylet hub 5 and the tube 7, which have properties for permitting visual confirmation thereof.

After such confirmation, the outer needle 2 and the stylet 4 are further advanced a minute distance in the tip direction.

In addition, when the blood vessel is punctured in this manner, priming of the inner cavity 21 of the outer needle 2 with the infusion liquid has already been completed, so that erroneous penetration of bubbles into the blood vessel is reliably prevented, and extremely high safety is ensured.

Further, as mentioned above, in the indwelling needle assembly 1 according to the present invention, in the assembled condition where the tube 7 is connected to the base end part of the outer needle hub 3, the center axis $O_1$ of the outer needle 2 and the center axis $O_2$ of the tube 7 at the tip part thereof are substantially parallel with each other. Therefore, at the time of puncturing with the outer needle 2 and the stylet 4, the tube 7 does not present an obstacle, and excellent operability is ensured.

[4] When the blood vessel is accessed by the outer needle 2, either the outer needle 2 or the outer needle hub 3 is fixed by one hand, while the stylet hub 5 is pulled in the base direction by gripping it with the other hand, to evulse the stylet 4 from the outer needle 2.

[5] When the stylet 4 is further moved in the base direction and the needlepoint 41 has passed through the slit 81, the slit 81 in the seal member 8 closes. This ensures that leakage of liquid through the slit 81 is prevented, and asepsis at the inside of the outer needle hub 3 and the infusion line is secured.

[6] When the stylet 4 is further moved in the base direction and the needlepoint 41 passes through the vicinity of the recessed part 912 of the stylet passage 911, the shutter member 921 is moved toward the side of the stylet passage 911 under pushing by the coil spring 922, and the righthand surface of the shutter member 921 is brought into contact with a surface opposed to the recessed part 912 of the stylet passage 911. Namely, the shutter means 92 is transferred from the first posture (see FIG. 2) to the second posture (see FIG. 4).

When the shutter means 92 is placed in the second posture, the shutter member 921 closes the stylet passage 911. Therefore, even if the needlepoint 41 tends to return again in the tip direction, the needlepoint 41 abuts against the shutter member 921 and cannot return.

[7] When the stylet 4 is further moved in the base direction and the needlepoint 41 passes through the vicinity of the through-hole 913 of the inner needle passage 911, the fixing pin 10 is moved toward the side of the stylet passage 911 under pushing by the coil spring 12, and the righthand surface of the fixing pin 10 abuts against a surface opposed to the through-hole 913 of the stylet passage 911. In this instance, the lefthand end part of the fixing pin 10 comes off from the through-hole 35 of the outer needle hub 3. As a result, fixation of the protector 9 to the outer needle hub 3 is cleared (see FIG. 5).

In such a condition, in which fixation of the protector 9 to the outer needle hub 3 is cleared, the shutter means 92 operates assuredly. Therefore, an accident wherein a worker erroneously punctures his or her finger or the like with the needlepoint 41 when discarding the stylet 4, or on similar occasions, can be prevented more securely.

[8] When the stylet 4 is further moved toward the base direction, the first varied outer diameter section 42 cannot pass through the reduced diameter part 915 and engages with the reduced diameter part 915 (i.e., the stylet 4 becomes engaged with the protector 9).

When the stylet hub 5 is further pulled in the base direction in this condition, the protector 9 engaged with the stylet 4 is moved in the base direction together with the stylet 4, and becomes separated from the outer needle hub 3 (see FIGS. 6 and 7). In this instance, the connection member 20 prevents the protector 9 from coming off from the stylet hub 5.

Incidentally, also at the time of carrying out the series of operations in the aforementioned steps [5] to [9], the center axis $O_1$ of the outer needle 2 and the center axis of the tube 7 at the tip side are kept substantially parallel with each other by the guides 523 of the stylet hub 5, so that these operations can be carried out smoothly and assuredly.

[9] Next, the tube 7 inserted into the stylet hub 5 is detached through the gap 521 (see FIG. 8).

After the stylet 4 has been evulsed from the outer needle 2, the stylet 4 and the stylet hub 5 are useless and, therefore, are discarded.

The stylet 4 has the needlepoint 41 thereof covered by the protector 9, and, particularly, the needlepoint 41 cannot be moved toward the tip side beyond the shutter means 92 and protrude from the tip of the protector 9. Therefore, an accident in which a worker discarding the stylet 4, or a similar person, erroneously punctures his or her finger or the like with the needlepoint 41 is prevented.

[10] Next, the vanes 6a and 6b are opened and are fixed to the patient's skin by use of a pressure sensitive adhesive tape or the like, closure of the tube 7 or the infusion line by the clamp is cleared, and supply of the infusion liquid is started.

The infusion liquid supplied from the infusion line is fed through the inner cavities of the connector 72, the tube 7, the outer needle hub 3, and the outer needle 2, into the patient's blood vessel.

Second Embodiment

Figure 9:
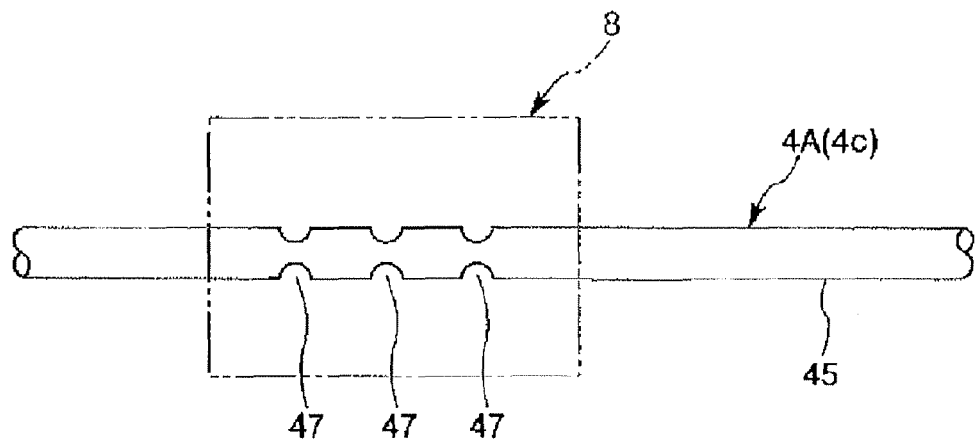
FIG. 9 is a plan view of a stylet possessed by the indwelling needle assembly of the present invention (second embodiment)

FIG. 9 is a plan view of a stylet possessed by an indwelling needle assembly according to the present invention (second embodiment).

The second embodiment of the indwelling needle assembly of the present invention shall be described below referring to this figure. The following descriptions will be centered on differences of the present embodiment from the above-described embodiment, and descriptions of the same items will be omitted.

The present embodiment is the same as the first embodiment above, except for the shape of the stylet (i.e., the configuration of the movement suppressing means).

As shown in FIG. 9, a minimum outer diameter section 4c of a stylet 4A is provided with three reduced diameter parts (varied outer diameter parts) 47 thereon, where the outer diameter of the minimum outer diameter section 4c is reduced. Each of the reduced diameter parts 47 forms a part that is provided on the outside surface 45 of the minimum outer diameter section 4c of the stylet 4A, and at which the outer diameter of the minimum outer diameter section 4c (stylet 4) is abruptly varied (reduced). That is, the reduced diameter parts 47 are each formed by ring-shaped recessed parts.

In addition, the three reduced diameter parts 47 are provided at intervals along the longitudinal direction of the stylet 4A.

With such reduced diameter parts 47, the area of contact between the stylet 4A (inclusive of the reduced diameter parts 47) and the inside surface 811 of a slit 81 is enlarged, as compared with a case in which the reduced diameter parts 47 are absent. As a result, when a puncturing operation is carried out by pinching the vanes 6a and 6b with the fingertips in an assembled condition of the indwelling needle assembly 1, frictional resistance between the outside surface 45 of the stylet 4A and the inside surface 811 of the slit 81 is increased. Therefore, a problem wherein the stylet 4A is pushed by the skin and retracted into an outer needle 2 before the skin is punctured is prevented or restrained, so that the stylet 4A punctures the skin assuredly. In other words, the indwelling needle assembly 1 exhibits excellent operability at the time of the puncturing operation.

Thus, the reduced diameter parts 47 function as movement suppressing means, for inhibiting or suppressing movement of the stylet 4A relative to a seal member 8 when the vanes 6a and 6b are operated in the assembled condition.

Incidentally, the reduced diameter parts 47 may be formed by working (i.e., performing cutting) after the minimum outer diameter section 4c has been formed, for example.

In addition, the number of the reduced diameter parts 47 formed (disposed) is not limited to three. The number may be one, two, or four or more.

Third Embodiment

Figure 10:
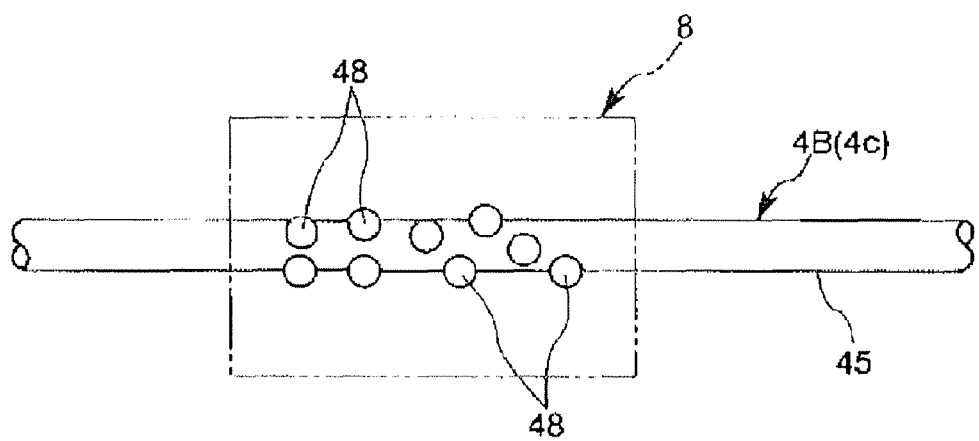
FIG. 10 is a plan view of a stylet possessed by the indwelling needle assembly of the present invention (third embodiment)

FIG. 10 is a plan view of a stylet possessed by an indwelling needle assembly according to the present invention (third embodiment).

The third embodiment of the indwelling needle assembly of the present invention shall be described below referring to this figure. The following descriptions will be centered on differences of the present embodiment from the above-described embodiments, and descriptions of the same items will be omitted.

The present embodiment is the same as the first embodiment above, except for the shape of the stylet (i.e., the configuration of the movement suppressing means).

As shown in FIG. 10, a minimum outer diameter section 4c of a stylet 4B is provided with a plurality of minute projecting parts (varied outer diameter parts) 48 thereon, which project from the outside surface 45 of the minimum outer diameter section 4c. Each of the projecting parts 48 forms a part that is provided on the outside surface 45 of the minimum outer diameter section 4c of the stylet 4A, and at which the outer diameter of the minimum outer diameter section 4c (stylet 4) is locally varied (increased) abruptly. That is, the projecting parts 48 are dome-shaped (spherical) parts.

In addition, the projecting parts 48 are disposed at random on the outside surface 45 of the stylet 4A.

With such projecting parts 48, the area of contact between the stylet 4B (the outside surface 45 inclusive of the projecting parts 48) and the inside surface 811 of a slit 81 is increased, as compared with the case in which the projecting parts 48 are absent. As a result, when a puncturing operation is carried out by pinching the vanes 6a and 6b with the fingertips in an assembled condition of the indwelling needle assembly 1, frictional resistance between the outside surface 45 of the stylet 4B and the inside surface 811 of the slit 81 is increased. Therefore, a problem wherein the stylet 4B is pushed by the skin and retracted into an outer needle 2 before the skin is punctured is prevented or restrained, so that the stylet 4B punctures the skin assuredly. In other words, the indwelling needle assembly 1 exhibits excellent operability at the time of the puncturing operation.

Thus, the projecting parts 48 function as a movement suppressing means for inhibiting or suppressing movement of the stylet 4B relative to a seal member 8 when the vanes 6a and 6b are operated in the assembled condition. Incidentally, the movement suppressing means in the embodiment may include roughening of the outside surface 45 of the minimum outer diameter section 4c of the stylet 4B.

In addition, each of the projecting parts 48 may be formed integrally with the stylet 4B. Alternatively, the projecting parts 48 may be prepared separately from the stylet 4B and then disposed (provided) on the stylet 4B by securing (for example, by welding) such separate components (i.e., the projecting parts 48) to the stylet 4B.

Fourth Embodiment

Figure 11:
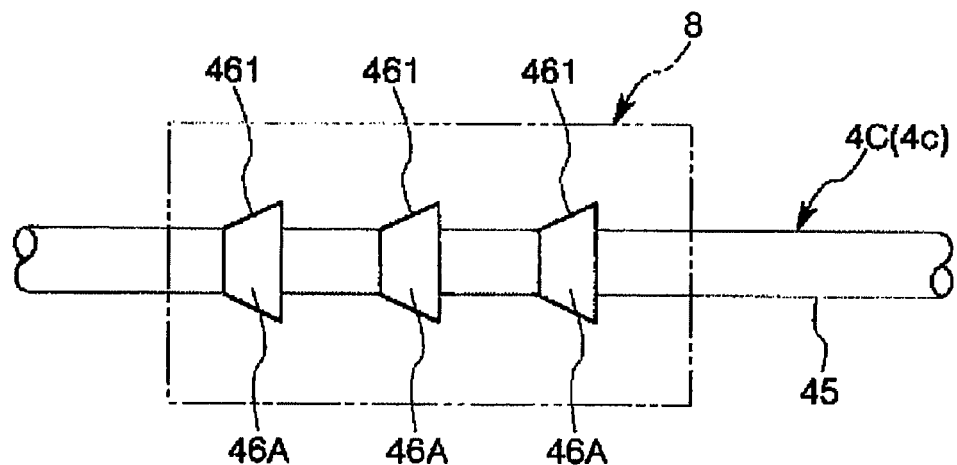
FIG. 11 is a plan view of a stylet possessed by the indwelling needle assembly of the present invention (fourth embodiment)

FIG. 11 is a plan view of a stylet possessed by an indwelling needle assembly according to the present invention (fourth embodiment). Incidentally, the righthand side in FIG. 11 will be referred to as "the base", whereas the lefthand side will be referred to as "the tip" in the following descriptions.

The fourth embodiment of the indwelling needle assembly of the present invention shall be described below. The following descriptions will be centered on differences of the present embodiment from the above-described embodiments, and descriptions of the same items will be omitted.

The present embodiment is the same as the first embodiment above, except for the shape of the enlarged diameter parts (i.e., the configuration of the movement suppressing means).

As shown in FIG. 11, each of the enlarged diameter parts 46A of a stylet 4C has a tip surface 461 that is inclined relative to the center axis of the stylet 4C, i.e., which is tapered. This ensures that the stylet 4C is more liable to move in the tip direction, while being less liable to move in the base direction. In other words, the extent of inhibition or suppression of movement of the stylet 4C differs, depending on whether the movement of the stylet 4C is a distal movement or a proximal movement.

With such enlarged diameter parts 46A, it is possible for the stylet 4C to be inserted easily into a seal member 8, for example, when placing the indwelling needle assembly 1 in an assembled condition (i.e., when manufacturing the indwelling needle assembly 1). In addition, when a puncturing operation is conducted by pinching the vanes 6a and 6b in an assembled condition of the indwelling needle assembly 1, a problem wherein the stylet 4C is pushed by the skin and retracted into an outer needle 2 before the skin is punctured is prevented or restrained, so that the stylet 4C punctures the skin assuredly.

Incidentally, although the number of enlarged diameter parts 46A is three according to the embodiment illustrated in the figure, the invention is not limited to such a configuration. The number of enlarged diameter parts 46A may be one, two, or four or more.

Fifth Embodiment

Figure 12:
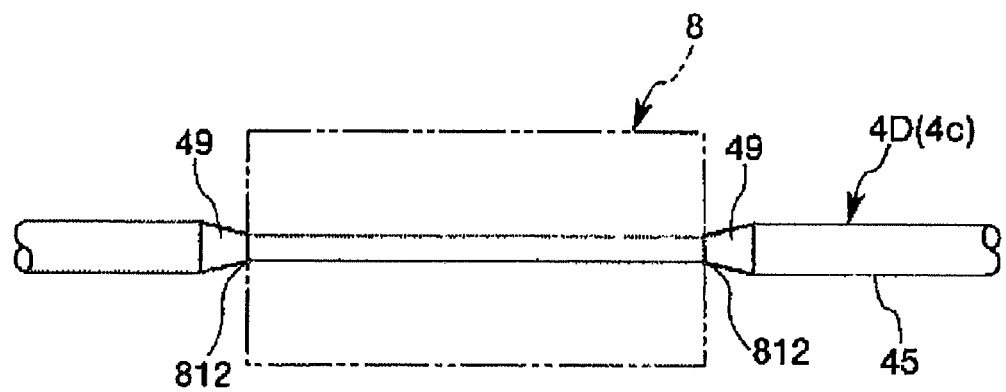
FIG. 12 is a plan view of a stylet possessed by the indwelling needle assembly of the present invention (fifth embodiment)
Figure 13:
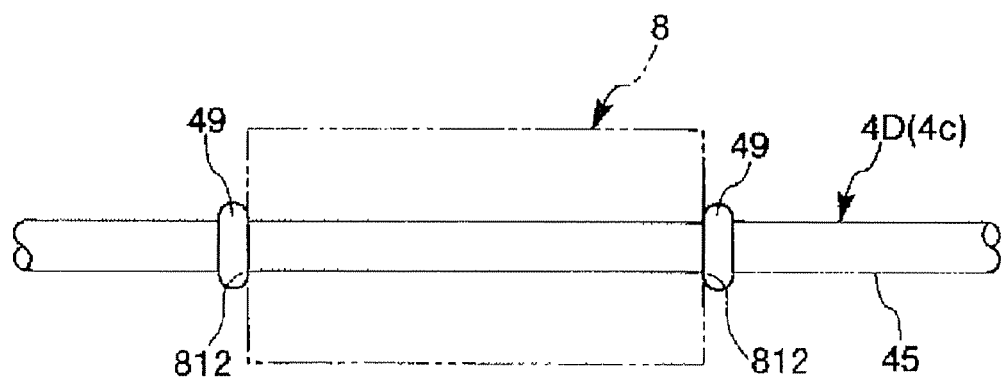
FIG. 13 is a plan view of a stylet possessed by the indwelling needle assembly of the present invention (fifth embodiment)

FIGS. 12 and 13 are plan views of a stylet possessed by an indwelling needle assembly according to the present invention (fifth embodiment). Incidentally, the righthand side in FIGS. 12 and 13 will be referred to as "the base", and the left side as "the tip" in the following descriptions.

The fifth embodiment of the indwelling needle assembly of the present invention shall be described below referring to these figures. The following descriptions will be centered on differences of the present embodiment from the above-described embodiments, and descriptions of the same items will be omitted.

The present embodiment is the same as the first embodiment above, except for the shape of the stylet (i.e., the configuration of the movement suppressing means).

As shown in FIG. 12, a minimum outer diameter section 4c (outside surface 45) of a stylet 4D is provided with stepped parts (engaging parts) 49 thereon, where the outer diameter differs (varies). The stepped parts 49 engage with edge parts 812 of a slit 81 in the assembled condition.

With such stepped parts 49, when a puncturing operation is conducted by pinching the vanes 6a and 6b with the fingertips in an assembled condition of the indwelling needle assembly 1, it is ensured that the edge part 812 on the tip side (the lefthand side in FIG. 12) and the stepped part 49 on the tip side engage with (i.e., abut against) each other. Therefore, a problem wherein the stylet 4D is pushed by the skin and retracted into an outer needle 2 before the skin is punctured is prevented or restrained, so that the stylet 4D can puncture the skin assuredly.

Thus, the stepped parts 49 function as a movement suppressing means for inhibiting or suppressing movement of the stylet 4D relative to a seal member 8, when the vanes 6a and 6b are operated in the assembled condition.

Incidentally, the stepped parts 49 are not limited to the configuration shown in FIG. 12, in which the portion corresponding to the seal member 8 (slit 81) is reduced in diameter. For example, the configuration shown in FIG. 13, in which portions corresponding to the vicinity of edge parts 812 of the seal member 8 are enlarged in diameter, may also be adopted.

Sixth Embodiment

Figure 15:
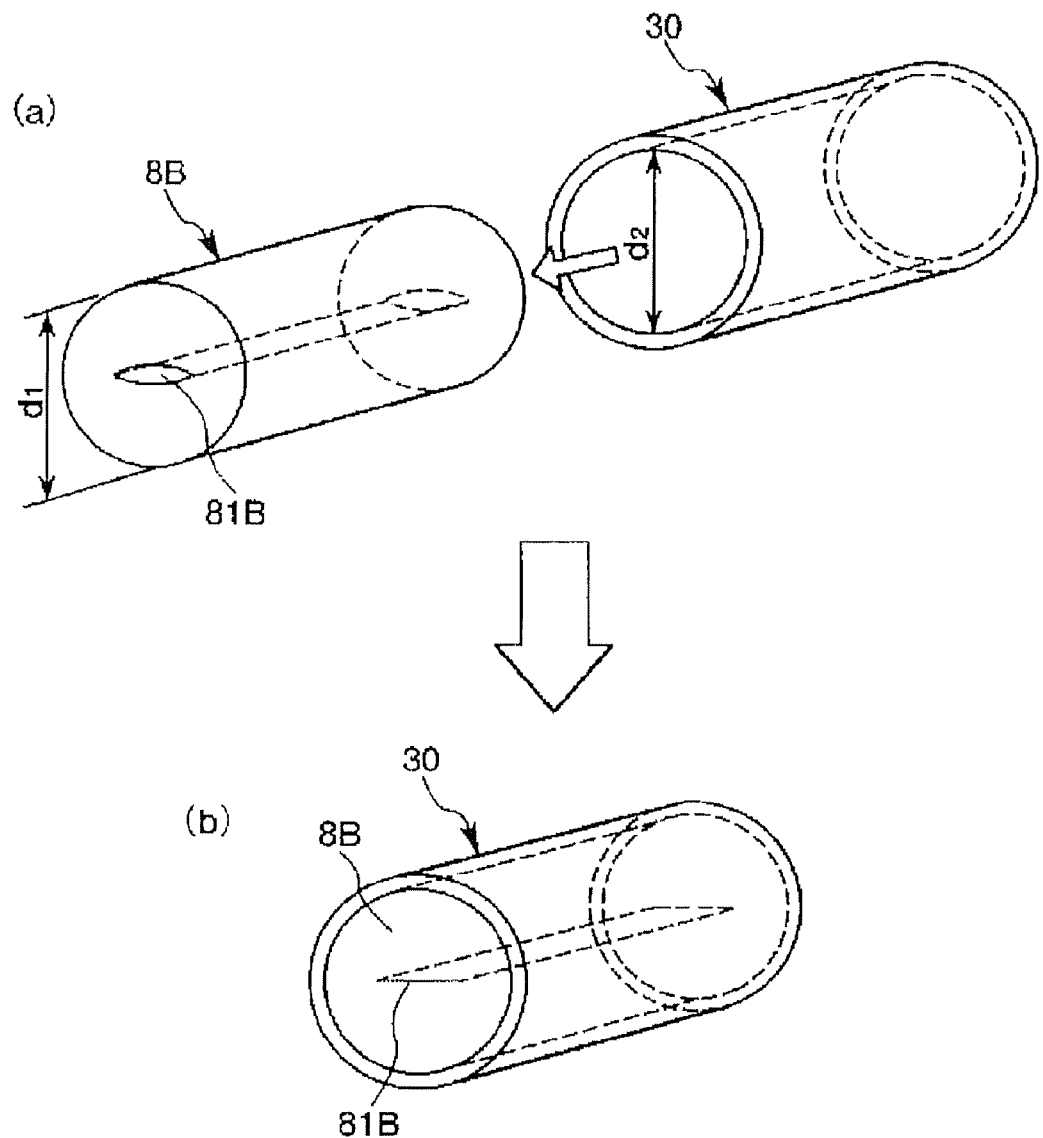
FIG. 15 is a perspective view of a seal member and a compression member, which are possessed by the indwelling needle assembly of the present invention (sixth embodiment).

FIG. 15 shows perspective views of a seal member and a compression member, which are possessed by an indwelling needle assembly according to the present invention (sixth embodiment).

The sixth embodiment of the indwelling needle assembly of the present invention shall be described below referring to this figure. The following descriptions will be centered on differences of the present embodiment from the above-described embodiments, and descriptions of the same items will be omitted.

The present invention is the same as the first embodiment above, except for the configuration of the seal member.

The seal member 8B shown in FIG. 15(*a*) has a hole 81B therein, which is open in the natural condition. Herein, the term "natural condition" implies a condition in which no external force is exerted on the seal member 8B.

In the indwelling needle assembly 1 according to this embodiment, the seal member 8B is contained under pressure inside of a compression member 30, which is composed of a tubular body disposed on the outer needle hub 3 in this condition (see FIG. 15(*b*)).

The seal member 8B is contained under pressure in the compression member 30, whereby the seal member 8 is compressed in a direction that closes the hole 81B, i.e., in the radial direction. As a result, the hole 81B is closed assuredly.

Incidentally, the outer diameter $d_1$ of the seal member 8 is set to be slightly larger than the inner diameter $d_2$ of the compression member 30. This ensures that the seal member 8 is compressed securely in the radial direction, and that the hole 81B therefore is closed assuredly. In addition, friction between the outside surface 45 of a stylet 4 and the inside surface 811 of the hole 81B is increased. Therefore, a problem wherein the stylet 4 is pushed by the skin and retracted into an outer needle 2 before the skin is punctured is prevented or restrained, so that the stylet 4 punctures the skin without fail. Moreover, in this embodiment, the hole 81B is configured as a slit, whereby the effect thereof is obtained more assuredly.

While the indwelling needle assembly according to the present invention has been described with reference to the embodiments shown in the drawings, the invention is not limited to these embodiments. Various components or parts of the indwelling needle assembly can be replaced by other components or parts having arbitrary configurations, but which can exhibit functions that are the same as or equivalent to the above-mentioned functions. Further, arbitrary structures may be added to the above-described embodiments.

In addition, the indwelling needle assembly of the present invention may be constituted as an arbitrary combination of the configurations (characteristic features) of two or more of the above-described embodiments.

For example, the minimum outer diameter section of the stylet according to the first embodiment may be further provided with the reduced diameter parts, similar to those provided on the minimum outer diameter section of the stylet of the second embodiment, or may be further provided with the projecting parts provided on the minimum outer diameter section of the stylet of the third embodiment.

Further, the minimum outer diameter section of the stylet according to the fifth embodiment may be further provided with enlarged diameter parts, similar to those provided on the minimum outer diameter section of the stylet of the first embodiment, or with the reduced diameter parts provided on the minimum outer diameter section of the stylet of the second embodiment, or with the projecting parts provided on the minimum outer diameter section of the stylet of the third embodiment.

In addition, the indwelling needle assembly according to the present invention is not limited to being used in a condition of being inserted into a blood vessel. The indwelling needle assembly is applicable also to being used in a condition of being inserted, for example, into the abdominal cavity, the thoracic cavity, a lymph vessel, the vertebral canal, or the like.

The shape of the slit in the seal member is not limited to a straight line segment, and the slit may have, for example, a cross (+) shape, a Y shape, a T shape, or an H shape.

The configuration of the movement suppressing means is not limited to those described in the above embodiments. For example, a configuration may be adopted based on utilization of a blockage between the outside surface of the stylet and the inside surface of a hole or slit in the seal member. In addition, such a blockage may be combined with one of the aforementioned movement suppressing means described in the above embodiments. Such a blockage ensures that a problem, in which the stylet is pushed by the skin and is retracted into the outer needle before piercing the skin, can be prevented or restrained, so that the stylet can reliably puncture the skin without fail.

Herein, the term "blockage" signifies a mutual sticking due to tackiness between the outside surface of the stylet and the inside surface of the hole or slit in the seal member, or a mutual sticking under pressure between the outside surface of the stylet and the inside surface of the hole or slit in the seal member.

In addition, a cap may be provided, which is mounted on the base end part of the outer needle hub after the stylet has been evulsed from the outer needle. This ensures that leakage of liquid through the base of the outer needle hub can be prevented more securely. The cap may be formed integrally with the outer needle hub, or may be formed as a separate body apart from the outer needle hub. The method for fixing the cap to the outer needle hub may be any method, such as a method based on friction, a method based on hooking, etc.

In addition, the protector is not limited to the configurations shown in the figures. For example, a protector may be provided, which is turnable (displaceable) between a position where it covers at least the needlepoint of the stylet, and another position where the protector is spaced from the stylet.

Further, the connector provided at the end part of the tube is not particularly limited. Examples of a connector which can be used include a needleless connector, as described in Japanese Laid-Open Patent Publication No. 2005-261931, a three-way cock, etc.

In addition, the component provided at the end part of the tube is not limited to the above-mentioned connector. For example, a cap, an air filter, or the like, may also be adopted.

Further, in the indwelling needle assembly according to the present invention, the connector, the cap, and the air filter may be attached in a switchable manner, as required, to the end part of the tube.

INDUSTRIAL APPLICABILITY

The indwelling needle assembly according to the present invention includes a stylet having a sharp needlepoint at the tip thereof, a stylet hub secured to a base end part of the stylet, a hollow outer needle in which the stylet is inserted, an outer needle hub secured to a base end part of the outer needle, an opening formed at a base end part or a side part of the outer needle hub so as to communicate with the inner cavity of the outer needle, a seal member, which is fitted onto the outer needle hub and in which a hole or a slit for insertion of the stylet therein is formed so as to become closed when the inserted stylet is extracted, an operating part installed on the outer needle hub for enabling movement of the stylet and the outer needle along a longitudinal direction when the stylet is inserted into the outer needle, and movement suppressing means for inhibiting or suppressing movement of the stylet relative to the seal member when the operating part is operated. Therefore, when a puncturing operation is performed, movement of the stylet can be inhibited or restrained assuredly, so that the stylet punctures the skin without fail. In other words, the indwelling needle assembly is excellent in operability (ease of manipulation), whereby a line for infusion or the like can be secured easily and assuredly. Accordingly, the puncture implement of the present invention has industrial applicability.

The invention claimed is:

1. An indwelling needle assembly comprising:
a hollow outer needle possessing a base end part, a distal tip and an inner cavity, the outer needle being dimensioned to puncture and be positioned in a patient's blood vessel;
an outer needle hub secured to the base end part of the outer needle, the outer needle hub having an interior and an inner surface surrounding the interior;
a stylet possessing an outer surface, a tip end, and a base end part, with a sharp needlepoint at the tip of the stylet, the stylet being positioned inside the hollow outer needle and extending through the interior of the outer needle hub, the stylet being positionable relative to the needle to expose the sharp needlepoint distally beyond the distal tip of the outer needle, the sharp needlepoint being configured to puncture the patient's blood vessel when the sharp needlepoint is positioned distally beyond the distal tip of the outer needle;
a stylet hub secured to the base end part of the stylet;
an opening at a base end part or a side part of the outer needle hub, the opening communicating with the inner cavity of the outer needle;
a seal member positioned in the interior of the outer needle hub, the seal member possessing an outer surface facing the inner surface of the outer needle hub, the seal member comprising a hole or slit extending completely through the seal member, the stylet extending completely through the slit or hole in the seal member, the stylet being removable from the seal member, the slit or hole automatically closing when the stylet is removed from the seal member, the slit or hole possessing an inner surface;
an operating part disposed on the outer needle hub to enable movement of the stylet and the outer needle together in a longitudinal direction to puncture the patient's blood vessel;
movement suppressing means for preventing or restraining the stylet from retracting into the outer needle by inhibiting or suppressing movement of the stylet relative to the seal member when the operating part is operated;
wherein said movement suppressing means comprises a varied outer diameter part on the outside surface of said stylet, wherein an outer diameter of said stylet varies abruptly, such that frictional resistance between the outside surface of said stylet and the inner surface of said hole or slit is increased;
wherein said movement suppressing means is positioned to make contact with said hole or slit in the inserted condition of the stylet;
wherein the seal member includes a through conduit passing completely through the seal member, the through conduit being fluidly in communication with the opening, the opening being connected to a tube; and
wherein the tube extends through the stylet hub.

2. The indwelling needle assembly as set forth in claim 1, wherein said movement suppressing means is configured such that an extent of inhibition or suppression of the movement of the stylet differs depending on whether the movement of the stylet is in a distal direction or a proximal direction.

3. The indwelling needle assembly as set forth in claim 1, wherein the movement suppressing means comprises an enlarged engaging part disposed on an outside surface of the stylet and engaging an edge part of the hole or slit in the inserted condition, the enlarged engaging part having an outer dimension greater than an outer dimension of a portion of the stylet immediately adjoining the enlarged engaging part that is devoid of the enlarged engaging part.

4. The indwelling needle assembly as set forth in claim 1, wherein said movement suppressing means comprises a blockage disposed between an outside surface of the stylet and an inside surface of the hole or slit in the seal member.

5. The indwelling needle assembly as set forth in claim 1, further comprising a compression member in which the seal member is positioned, the compression member applying a compression force to the seal member closing the hole or slit in the seal member.

6. The indwelling needle assembly as set forth in claim 1, further comprising a protector covering at least the needlepoint of the stylet when the stylet is extracted from the outer needle.

7. The indwelling needle assembly as set forth in claim 1, wherein the seal member possesses a conduit spaced apart from the hole or slit, the conduit possessing opposite ends which open to outside the seal member.

8. The indwelling needle assembly as set forth in claim 1, wherein the seal member possesses an outer surface and opposite axial endmost portions, the outer surface of the opposite axial endmost portions of the seal member contacting the inner surface of the outer needle hub.

* * * * *